(12) United States Patent
Nerenberg et al.

(10) Patent No.: US 6,232,318 B1
(45) Date of Patent: May 15, 2001

(54) PYRIMIDINEDIONE DERIVATIVES USEFUL AS ALPHA 1A ADRENOCEPTOR ANTAGONISTS

(75) Inventors: Jennie B. Nerenberg, Maple Glen; Mark G. Bock, Hatfield, both of PA (US)

(73) Assignee: Merck & Co., Ltd., Rahway, NJ (US)

( * ) Notice: Subject to any disclaimer, the term of this patent is extended or adjusted under 35 U.S.C. 154(b) by 0 days.

(21) Appl. No.: 09/438,798

(22) Filed: Nov. 12, 1999

Related U.S. Application Data

(60) Provisional application No. 60/108,146, filed on Nov. 12, 1998.

(51) Int. Cl.[7] ............... C07D 401/12; C07D 401/06; A61K 31/4545
(52) U.S. Cl. ............... 514/274; 544/310; 544/311; 544/312; 544/313; 544/314; 544/309
(58) Field of Search ............... 514/210.2, 211.15, 514/270, 274; 540/354, 355, 362, 363, 364, 601; 544/299, 300, 301, 302, 303, 304, 311, 312, 316

(56) References Cited

U.S. PATENT DOCUMENTS

| | | | |
|---|---|---|---|
| 4,661,491 | 4/1987 | Regnier | 514/260 |
| 5,859,014 * | 1/1999 | Bantle et al. | 514/255 |

FOREIGN PATENT DOCUMENTS

| | | |
|---|---|---|
| 748800 | 12/1996 | (EP) . |
| WO 92/00073 | 1/1992 | (WO) . |
| WO 92/16213 | 10/1992 | (WO) . |
| WO 94/08040 | 4/1994 | (WO) . |
| WO 94/10989 | 5/1994 | (WO) . |
| WO 94/22829 | 10/1994 | (WO) . |
| WO 96/14846 * | 5/1996 | (WO) . |
| WO 96/40135 | 12/1996 | (WO) . |
| WO 97/17969 | 5/1997 | (WO) . |
| WO 97/42956 | 11/1997 | (WO) . |

OTHER PUBLICATIONS

Kumar et al., Design Synthesis and Biological Evaluation of 1,3–Diaminopropanes: A New Class of Polyamine Analogs as Leishmanicidal Agents. Bioorg. Med. Chem. Lett. 7(6), p. 675–680, 1997.*

Michel et al., Classification of alpha 1–adrenoceptor subtypes, Naunyn–Schmiedeberg's Arch. Pharmacol., (1995) 352:1–10.

* cited by examiner

*Primary Examiner*—Richard L. Raymond
*Assistant Examiner*—Deepak R. Rao
(74) *Attorney, Agent, or Firm*—Catherine D. Fitch; Kenneth R. Walton; Melvin Winokur

(57) ABSTRACT

Novel pyrimidinedione compounds and pharmaceutically acceptable salts thereof are disclosed. The synthesis of these compounds and their use as alpha 1a adrenergic receptor antagonists is also described. One application of these compounds is in the treatment of benign prostatic hyperplasia. These compounds are selective in their ability to relax smooth muscle tissue enriched in the alpha 1a receptor subtype without at the same time inducing hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia can be achieved.

37 Claims, No Drawings

PYRIMIDINEDIONE DERIVATIVES USEFUL AS ALPHA 1A ADRENOCEPTOR ANTAGONISTS

This application claims the benefit of U.S. Provisional Application No. 60/108,146, filed Nov. 12, 1998.

FIELD OF THE INVENTION

This invention relates to certain pyrimidinedione compounds and pharmaceutically acceptable salts thereof, their synthesis, and their use as alpha 1a adrenoceptor antagonists. More particularly, the compounds of the present invention are useful for treating benign prostatic hyperplasia (BPH).

References are made throughout this application to various publications, the disclosures of which are hereby incorporated by reference in their entireties, in order to more fully describe the state of the art to which this invention pertains.

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, $\beta_1$, and $\beta_2$ subtypes. Functional differences between alpha 1 and alpha 2 receptors have been recognized, and compounds which exhibit selective binding between these two subtypes have been developed.

For a general background on the alpha adrenergic receptors, the reader's attention is directed to Robert R. Ruffolo, Jr., α-*Adrenoreceptors: Molecular Biology, Biochemistry and Pharmacology*, (*Progress in Basic and Clinical Pharmacology* series, Karger, 1991), wherein the basis of alpha 1/alpha 2 subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting alpha-adrenergic receptor affinity was explored.

The cloning, sequencing and expression of alpha receptor subtypes from animal tissues has led to the subclassification of the alpha 1 receptors into alpha 1d (formerly known as alpha 1a or 1a/1d), alpha 1b and alpha 1a (formerly known as alpha 1c) subtypes. Each alpha 1 receptor subtype exhibits its own pharmacologic and tissue specificities. The designation "alpha 1a" is the appellation recently approved by the IUPHAR Nomenclature Committee for the previously designated "alpha 1c" cloned subtype as outlined in the 1995 Receptor and Ion Channel Nomenclature Supplement (Watson and Girdlestone, 1995). The designation alpha 1a is used throughout this application to refer to this subtype. At the same time, the receptor formerly designated alpha 1a was renamed alpha 1d. The new nomenclature is used throughout this application. Stable cell lines expressing these alpha 1 receptor subtypes are referred to herein; however, these cell lines were deposited with the American Type Culture Collection (ATCC) under the old nomenclature. For a review of the classification of alpha 1 adrenoceptor subtypes, see, Michel et al., *Naunyn-Schmiedeberg's Arch. Pharmacol.* (1995), 352:1–10.

The differences in the alpha adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concommitantly, the increased noradrenergic innervation of the enlarged prostate leads to an increased adrenergic tone of the bladder neck and urethra, further restricting the flow of urine through the urethra.

In benign prostatic hyperplasia, the male hormone 5alpha-dihydrotestosterone has been identified as the principal culprit. The continual production of 5α-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc.'s product PROSCAR® (finasteride). The effect of this compound is to inhibit the enzyme testosterone 5-α reductase, which converts testosterone into 5α-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the lower urinary tract tissue, by binding to alpha 1 adrenergic receptors, thus reducing the increased adrenergic tone due to the disease, would be good candidates for this activity. Thus, one such agent is alfuzosin, which is reported in EP 0 204597 to induce urination in cases of prostatic hyperplasia. Likewise, in WO 92/00073, the selective ability of the R(+) enantiomer of terazosin to bind to adrenergic receptors of the alpha 1 subtype was reported. In addition, in WO 92/16213, combinations of 5α-reductase inhibitory compounds and alphal-adrenergic receptor blockers (terazosin, doxazosin, prazosin, bunazosin, indoramin, alfuzosin) were disclosed. However, no information as to the alpha 1d, alpha 1b, or alpha 1a subtype specificity of these compounds was provided as this data and its relevancy to the treatment of BPH was not known. Current therapy for BPH uses existing non-selective alpha 1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha 1d and alpha 1b receptors in the peripheral vasculature, e.g., hypotension and syncope.

The relatively recent cloning of the human alpha 1a adrenergic receptor (ATCC CRL 11140) and the use of a screening assay utilizing the cloned human alpha 1a receptor has enabled identification of compounds which specifically interact with the human alpha 1a adrenergic receptor. For further description, see WO 94/08040 and WO 94/10989. As disclosed in the instant patent disclosure, a cloned human alpha 1a adrenergic receptor and a method for identifying compounds which bind the human alpha 1a receptor has made possible the identification of selective human alpha 1a adrenergic receptor antagonists useful for treating BPH.

Several classes of compounds have been disclosed to be selective alpha 1a adrenergic receptor antagonists useful for treating BPH. WO 94/22829 discloses, for example, certain 4-(un)substituted phenyl-1,4-dihydropyridine derivatives which are described as potent, selective alpha 1a antagonists with weak calcium channel antagonistic activity and which are further described to be anticipated as useful for treating BPH. As another example, WO 96/14846, WO 97/17969 and WO 97/42956 each disclose certain dihydropyrimidine derivatives (e.g., certain 1,2,3,6-tetrahydro-2-oxo-pyrimidine derivatives) which are selective antagonists for the human alpha 1a receptor and useful for treatment of BPH, impotency, cardiac arrhythmia, and other diseases where antagonism of the alpha 1a receptor may be useful. As still another example, WO 96/40135 discloses, inter alia, certain phenylpiperidinyl alkyl saccharin derivatives and their use as selective alpha 1a antagonists. Yet another example is EP 748800, which discloses, inter alia, certain arylpiperazinylpropyl substituted pyrimidinediones useful as alpha 1adrenoceptor antagonists.

The instant patent disclosure discloses novel pyrimidinedione compounds which selectively bind to the human alpha 1a receptor. These compounds are further tested for binding to other human alpha 1 receptor subtypes, as well as counterscreened against other types of receptors (e.g., alpha 2), thus defining the specificity of the compounds of the present invention for the human alpha 1a adrenergic receptor.

It is an object of the present invention to identify compounds which bind to the alpha 1a adrenergic receptor. It is a further object of the invention to identify compounds which act as antagonists of the alpha 1a adrenergic receptor. It is another object of the invention to identify alpha 1a adrenergic receptor antagonist compounds which are useful agents for treating BPH in animals, preferably mammals, especially humans. Still another object of the invention is to identify alpha 1a adrenergic receptor antagonists which are useful for relaxing lower urinary tract tissue in animals, preferably mammals, especially humans.

The compounds of the present invention are alpha 1a adrenergic receptor antagonists. Thus, the compounds of the present invention are useful for treating BPH in mammals. Additionally, it has been found that the alpha 1a adrenergic receptor antagonists of the present invention are also useful for relaxing lower urinary tract tissue in mammals.

SUMMARY OF THE INVENTION

The present invention provides pyrimidinedione compounds for the treatment of urinary obstruction caused by benign prostatic hyperplasia (BPH). The compounds antagonize the human alpha 1a adrenergic receptor at nanomolar and subnanomolar concentrations while exhibiting lower affinity for the alpha 1d and alpha 1b human adrenergic receptors and many other G-protein coupled receptors. This invention has the advantage over non-selective alpha 1adrenoceptor antagonists of reduced side effects related to peripheral adrenergic blockade. Such side effects include hypotension, syncope, lethargy, etc.

More particularly, the present invention is a compound of formula (I):

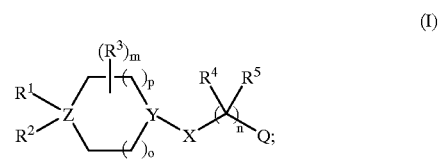

wherein Q is

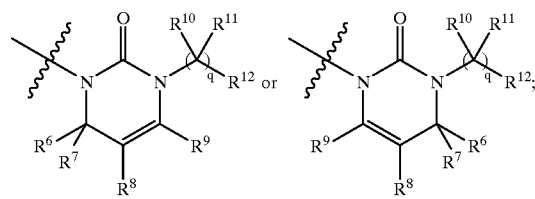

Z is C or N, provided that when Z is N, $R^2$ is absent;

X is $CR^aR^b$ or $NR^a$;

Y is CH or N; provided that when Y is N, Z is C and X is $CR^aR^b$; and provided that when Y is CH, X is $NR^a$;

$R^1$ is phenyl, mono- or poly-substituted phenyl, pyridyl, mono- or poly-substituted pyridyl, thienyl, or mono- or poly-substituted thienyl; wherein each of the substituents on the substituted phenyl is independently selected from halo, nitro, cyano, hydroxy, amino, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, $C(=O)N(R^c)_2$ and $SO_2N(R^c)_2$; each of the substituents on the substituted pyridyl is independently selected from halo, cyano, hydroxy, amino, $C_1$–$C_6$ alkyl, $C_1$–$C_6$ alkoxy, fluorinated $C_1$–$C_6$ alkyl, fluorinated $C_1$–$C_6$ alkoxy, $CO_2R^c$, $C(=O)N(R^c)_2$ and $SO_2N(R^c)_2$; and each of the substituents on the substituted thienyl is independently selected from halo, $C_1$–$C_6$ alkyl, and fluorinated $C_1$–$C_6$ alkyl;

$R^2$ is hydrogen, cyano, hydroxy, $CO_2R^c$, $C(=O)N(R^c)_2$, $NR^cC(=O)R^c$, $NR^cSO_2R^c$, phenyl, mono- or poly-substituted phenyl, pyridyl, mono- or poly-substituted pyridyl, thienyl, or mono- or poly-substituted thienyl; wherein each of the substituents on the substituted phenyl is independently selected from halo, nitro, cyano, hydroxy, amino, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, $C(=O)N(R^c)_2$ and $SO_2N(R^c)_2$; each of the substituents on the substituted pyridyl is independently selected from halo, cyano, hydroxy, amino, $C_1$–$C_6$ alkyl, $C_1$–$C_6$ alkoxy, fluorinated $C_1$–$C_6$ alkyl, fluorinated $C_1$–$C_6$ alkoxy, $CO_2R^c$, $C(=O)N(R^c)_2$ and $SO_2N(R^c)_2$; and each of the substituents on the substituted thienyl is independently selected from halo, $C_1$–$C_6$ alkyl, and fluorinated $C_1$–$C_6$ alkyl;

each $R^3$ is a substituent at a ring atom other than Z or Y and is independently $C_1$–$C_4$ alkyl;

$R^4$, $R^5$, $R^{10}$ and $R^{11}$ are each independently selected from hydrogen, $C_1$–$C_6$ alkyl, and $C_3$–$C_8$ cycloalkyl;

$R^6$ and $R^7$ are each independently selected from hydrogen, $C_1$–$C_6$ alkyl, and fluorinated $C_1$–$C_6$ alkyl; or $R^6$ and $R^7$ are taken together to form oxo;

$R^8$ and $R^9$ are each independently selected from hydrogen, halo, cyano, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, $C(=O)R^c$, $C(=O)N(R^c)_2$, phenyl, mono- or poly-substituted phenyl, pyridyl, mono- or poly-substituted pyridyl, thienyl, and mono- or poly-substituted thienyl; wherein each of the substituents on the substituted phenyl is independently selected from halo, nitro, cyano, hydroxy, amino, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, $C(=O)N(R^c)_2$ and $SO_2N(R^c)_2$; each of the substituents on the substituted pyridyl is independently selected from halo, cyano, hydroxy, amino, $C_1$–$C_6$ alkyl, $C_1$–$C_6$ alkoxy, fluorinated $C_1$–$C_6$ alkyl, fluorinated $C_1$–$C_6$ alkoxy, $CO_2R^c$, $C(=O)N(R^c)_2$ and $SO_2N(R^c)_2$; and each of the substituents on the substituted thienyl is independently selected from halo, $C_1$–$C_6$ alkyl, and fluorinated $C_1$–$C_6$ alkyl;

$R^{12}$ is hydrogen, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, phenyl, mono- or poly-substituted phenyl, pyridyl, mono- or poly-substituted pyridyl, thienyl, mono- or poly-substituted thienyl,

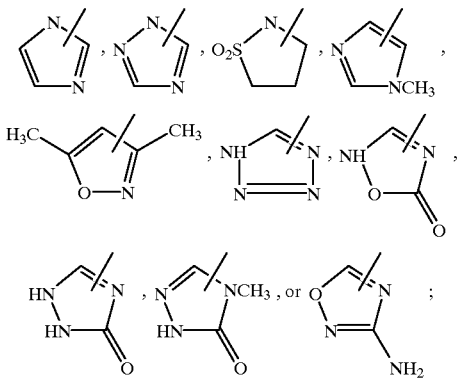

wherein each of the substituents on the substituted phenyl is independently selected from halo, nitro, cyano, hydroxy, amino, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, $C(=O)N(R^c)_2$ and $SO_2N(R^c)_2$; each of the substituents on the substituted pyridyl is independently selected from halo, cyano, hydroxy, amino, $C_1$–$C_6$ alkyl, $C_1$–$C_6$ alkoxy, fluorinated $C_1$–$C_6$ alkyl, fluorinated $C_1$–$C_6$ alkoxy, $CO_2R^c$, $C(=O)N(R^c)_2$ and $SO_2N(R^c)_2$; and each of the substituents on the substituted thienyl is independently selected from halo, $C_1$–$C_6$ alkyl, fluorinated $C_1$–$C_6$ alkyl;

$R^a$ and $R^b$ are each independently selected from hydrogen, $C_1$–$C_6$ alkyl, and $C_3$–$C_8$ cycloalkyl;

$R^c$ is hydrogen or $C_1$–$C_6$ alkyl;

m is an integer of from 0 to 4;

n is an integer of from 2 to 4, when X is $NR^a$;

n is an integer of from 1 to 3, when X is $CR^aR^b$;

o and p are each integers of from 0 to 2, wherein the sum of o+p is less than or equal to 3; and q is an integer of from 0 to 2;

or a pharmaceutically acceptable salt thereof.

The present invention also includes pharmaceutical compositions, methods of preparing pharmaceutical compositions, and methods of treatment.

These and other embodiments, aspects and features of the present invention are either further described in or will be apparent from the ensuing description, examples and appended claims.

DETAILED DESCRIPTION OF THE INVENTION

The present invention includes pyrimidinedione compounds of Formula (I) above. These compounds and their pharmaceutically acceptable salts are useful as alpha 1a antagonists.

In a first embodiment, the present invention is a compound of Formula (I), wherein $R^6$ and $R^7$ are taken together to form oxo;

and all other variables are as originally defined above; or a pharmaceutically acceptable salt thereof.

In a second embodiment, the present invention is a compound of Formula (I), wherein $R^1$ is phenyl; mono-, di- or tri-substituted phenyl; pyridyl; mono- or di-substituted pyridyl; thienyl; or mono-substituted thienyl;

$R^2$ is hydrogen, cyano, hydroxy, $CO_2R^c$, $C(=O)N(R^c)_2$, $NR^cC(=O)R^c$, $NR^cSO_2R^c$, phenyl, mono- or di- or tri-substituted phenyl, pyridyl, mono- or di-substituted pyridyl, thienyl, or mono-substituted thienyl;

$R^4$ and $R^5$ are either both hydrogen, or one of $R^4$ and $R^5$ is hydrogen and the other is hydrogen, $C_1$–$C_6$ alkyl, or $C_3$–$C_8$ cycloalkyl;

$R^8$ and $R^9$ are each independently selected from hydrogen, halo, cyano, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, $C(=O)R^c$, $C(=O)N(R^c)_2$, phenyl, mono- or di-substituted phenyl, pyridyl, mono- or di-substituted pyridyl, thienyl and mono-substituted thienyl; and $R^{10}$ and $R^{11}$ are either both hydrogen, or one of $R^{10}$ and $R^{11}$ is hydrogen and the other is hydrogen, $C_1$–$C_6$ alkyl, or $C_3$–$C_8$ cycloalkyl;

$R^{12}$ is hydrogen, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, phenyl, mono- or di-substituted phenyl, pyridyl, mono- or di-substituted pyridyl, thienyl, or mono-substituted thienyl,

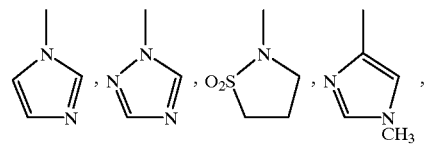

-continued

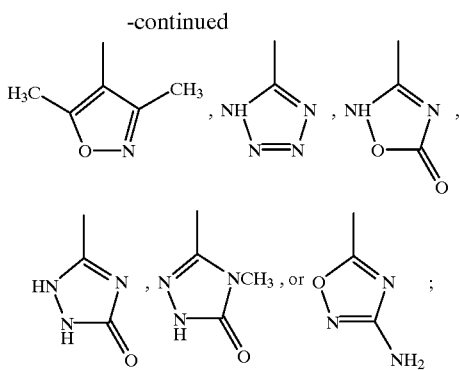

and all other variables are as originally defined above;
or a pharmaceutically acceptable salt thereof.

In a third embodiment, the present invention is a compound of Formula (I), wherein in $R^1$ each substituent on the substituted phenyl is independently selected from halo, nitro, cyano, hydroxy, amino, $C_1$–$C_4$ alkyl, $C_3$–$C_6$ cycloalkyl, $C_1$–$C_4$ alkoxy, fluorinated $C_1$–$C_4$ alkyl, fluorinated $C_3$–$C_6$ cycloalkyl, fluorinated $C_1$–$C_4$ alkoxy, $CO_2R^c$, $C(=O)N(R^c)_2$ and $SO_2N(R^c)_2$; each substituent on the substituted pyridyl is independently selected from halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$; and each substituent on the substituted thienyl is independently selected from halo and $C_1$–$C_4$ alkyl;

in $R^2$ each substituent on the substituted phenyl is independently selected from halo, nitro, cyano, hydroxy, amino, $C_1$–$C_4$ alkyl, $C_3$–$C_6$ cycloalkyl, $C_1$–$C_4$ alkoxy, fluorinated $C_1$–$C_4$ alkyl, fluorinated $C_3$–$C_6$ cycloalkyl, fluorinated $C_1$–$C_4$ alkoxy, $CO_2R^c$, $C(=O)N(R^c)_2$ and $SO_2N(R^c)_2$; each substituent on the substituted pyridyl is independently selected from halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$; and each substituent on the substituted thienyl is independently selected from halo and $C_1$–$C_4$ alkyl;

in $R^8$ and $R^9$ each substituent on the substituted phenyl is independently selected from halo, nitro, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$; each substituent on the substituted pyridyl is independently selected from halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$; and each substituent on the substituted thienyl is independently selected from halo and $C_1$–$C_4$ alkyl;

in $R^{12}$ each substituent on the substituted phenyl is independently selected from halo, nitro, cyano, hydroxy, amino, $C_1$–$C_4$ alkyl, $C_3$–$C_6$ cycloalkyl, $C_1$–$C_4$ alkoxy, fluorinated $C_1$–$C_4$ alkyl, fluorinated $C_3$–$C_6$ cycloalkyl, fluorinated $C_1$–$C_4$ alkoxy, $CO_2R^c$, $C(=O)N(R^c)_2$ and $SO_2N(R^c)_2$; each substituent on the substituted pyridyl is independently selected from halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$; and each substituent on the substituted thienyl is independently selected from halo and $C_1$–$C_4$ alkyl;

and all other variables are as defined above for the second embodiment;
or a pharmaceutically acceptable salt thereof.

In a fourth embodiment is a compound of Formula (I), wherein $R^6$ and $R^7$ are taken together to form oxo;
and all other variables are as defined above for the third embodiment;
or a pharmaceutically acceptable salt thereof.

In a fifth embodiment is a compound of Formula (I), wherein each of $R^4$, $R^5$, $R^{10}$ and $R^{11}$ is hydrogen;
m is 0;
and all other variables are as defined above for the fourth embodiment;
or a pharmaceutically acceptable salt thereof.

In a first class of the present invention is a compound of Formula (II):

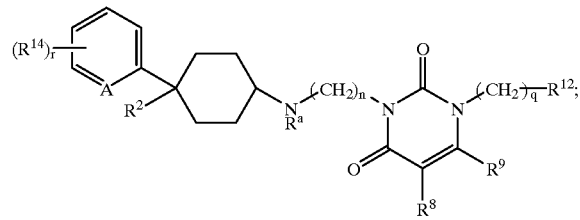

wherein A is C—$R^{14}$ or N;
$R^2$ is hydrogen, cyano, hydroxy, $CO_2R^c$, $C(=O)N(R^c)_2$, $NR^cC(=O)R^c$ or $NR^cSO_2R^c$;
$R^8$ and $R^9$ are each independently selected from hydrogen, halo, cyano, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)R^c$, $C(=O)N(R^c)_2$, phenyl, and mono- or di-substituted phenyl; wherein each substituent on the substituted phenyl is independently selected from fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ and $SO_2NH_2$;
$R^{12}$ is hydrogen, $C_1$–$C_4$ alkyl, $C_3$–$C_6$ cycloalkyl, $C_1$–$C_4$ alkoxy, fluorinated $C_1$–$C_4$ alkyl, fluorinated $C_1$–$C_4$ alkoxy, $CO_2R^c$, phenyl, or mono- or di-substituted phenyl; wherein each substituent on the substituted phenyl is independently selected from halo, nitro, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$;
each $R^{14}$ is independently hydrogen, halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ or $SO_2N(R^c)_2$;
$R^a$ is hydrogen or $C_1$–$C_6$ alkyl;
$R^c$ is hydrogen or $C_1$–$C_4$ alkyl;
n is an integer of from 2 to 4;
q is an integer of from 0 to 2; and
r is an integer of from 0 to 2;
or a pharmaceutically acceptable salt thereof.

Compounds exemplifying the invention include, but are not limited to, those selected from the group consisting of:
cis-4-[3-(5-methyl-2,6-dioxo-3,6-dihydro-2H-pyrimidin-1-yl)propylamino]-1-phenylcyclohexanecarbonitrile;
trans-4-[3-(5-methyl-2,6-dioxo-3,6-dihydro-2H-pyrimidin-1-yl)propylamino]-1-phenylcyclohexanecarbonitrile;

cis-(3-{3-[4-cyano4-(2-cyanophenyl)cyclohexylamino]
propyl}-5-methyl-2,4-dioxo-3,4-dihydro-2H-
pyrimidin-1-yl) acetic acid methyl ester;

cis-2-{1-cyano-4-[3-(3,5-dimethyl-2,6-dioxo-3,6-
dihydro-2H-pyrimidin-1-yl)propylamino]
cyclohexyl}benzonitrile;

cis-2-{1-cyano-4-[3-(3-cyclopropylmethyl-5-methyl-2,6-
dioxo-3,6-dihydro-2H-pyrimidin-1-yl)propylamino]
cyclohexyl}benzonitrile; and pharmaceutically acceptable salts thereof.

In a sub-class of the first class is a compound of Formula (II), wherein $R^{12}$ is of formula (III):

(III)

wherein each $R^{16}$ is independently hydrogen, fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ or $SO_2NH_2$;

q is 1;

s is an integer of from 0 to 2;

and all other variables are as defined above for the first class; or a pharmaceutically acceptable salt thereof.

Other compounds exemplifying the invention include, but are not limited to, those selected from the group consisting of:

trans-4-[3-(3-benzyl-5-methyl-2,6-dioxo-3,6-dihydro-
2H-pyrimidin-1-yl)propylamino]-1-(2,4-
difluorophenyl)cyclohexanecarbonitrile;

trans-4-[3-(3-benzyl-5-methyl-2,6-dioxo-3,6-dihydro-
2H-pyrimidin-1-yl)propylamino]-1-
phenylcyclohexanecarbonitrile;

1-benzyl-3-{3-[1-(4-fluoro-2-methoxyphenyl)piperidin-
4-ylamino]propyl}-5-methyl-1H-pyrimidine-2,4-
dione;

trans-1-benzyl-3-{3-[4-(2-methoxyphenyl)
cyclohexylamino]propyl}-5-methyl-1H-pyrimidine-2,
4-dione;

2-{4-[3-(3-benzyl-5-methyl-2,6-dioxo-3,6-dihydro-2H-
pyrimidin-1-yl)propylamino]cyclohexyl}benzonitrile;

trans-2-{4-[3-(3-benzyl-2,6-dioxo-5-phenyl-3,6-dihydro-
2H-pyrimidin-1-yl)propylamino]-1-
cyanocyclohexyl}benzonitrile; and pharmaceutically acceptable salts thereof.

In another sub-class of the first class is a compound of Formula (IV):

wherein $R^8$ is hydrogen, halo, cyano, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)R^c$, or $C(=O)N(R^c)_2$;

each $R^{16}$ is independently hydrogen, fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ or $SO_2NH_2$;

s is an integer of from 0 to 2;

and all other variables are as defined above for the first class; or a pharmaceutically acceptable salt thereof.

Still other compounds exemplifying the invention include, but are not limited to, those selected from the group consisting of:

cis-4-[3-(3-benzyl-5-methyl-2,6-dioxo-3,6-dihydro-2H-
pyrimidin-1-yl)propylamino]-1-(2,4-difluorophenyl)
cyclohexanecarbonitrile;

cis-4-[3-(3-benzyl-5-methyl-2,6-dioxo-3,6-dihydro-2H-
pyrimidin-1-yl)propylamino]-1-
phenylcyclohexanecarbonitrile;

cis-4-[3-(3-benzyl-5-methyl-2,6-dioxo-3,6-dihydro-2H-
pyrimidin-1-yl)propylamino]-1-(3,5-difluorophenyl)
cyclohexanecarbonitrile;

cis-4-[3-(3-benzyl-5-methyl-2,6-dioxo-3,6-dihydro-2H-
pyrimidin-1-yl)propylamino]-1-(2-methoxyphenyl)
cyclohexanecarbonitrile;

cis-4-[3-(3-benzyl-5-methyl-2,6-dioxo-3,6-dihydro-2H-
pyrimidin-1-yl)propylamino]-1-(2-
trifluoromethylphenyl)cyclohexanecarbonitrile;

cis-4-[3-(3-benzyl-5-methyl-2,6-dioxo-3,6-dihydro-2H-
pyrimidin-1-yl)propylamino]-1-(4-fluoro-2-
trifluoromethylphenyl)cyclohexanecarbonitrile;

cis-4-[3-(3-benzyl-5-methyl-2,6-dioxo-3,6-dihydro-2H-
pyrimidin-1-yl)propylamino]-1-(2,4-dichlorophenyl)
cyclohexanecarbonitrile;

cis-2-{4-[3-(3-benzyl-5-methyl-2,6-dioxo-3,6-dihydro-
2H-pyrimidin-1-yl)propylamino]-1-
cyanocyclohexyl}benzonitrile;

cis-4-[3-(3-benzyl-5-methyl-2,6-dioxo-3,6-dihydro-2H-
pyrimidin-1-yl)propylamino]-1-(2-
trifluoromethoxyphenyl)cyclohexanecarbonitrile;

cis-4-[3-(3-benzyl-5-methyl-2,6-dioxo-3,6-dihydro-2H-
pyrimidin-1-yl)propylamino]-1-pyridin-2-
ylcyclohexanecarbonitrile;

cis-2-{4-[3-(3-benzyl-2,6-dioxo-5-phenyl-3,6-dihydro-
2H-pyrimidin-1-yl)propylamino]-1-
cyanocyclohexyl}benzonitrile; and pharmaceutically acceptable salts thereof.

In a second class of the present invention is a compound of Formula (V):

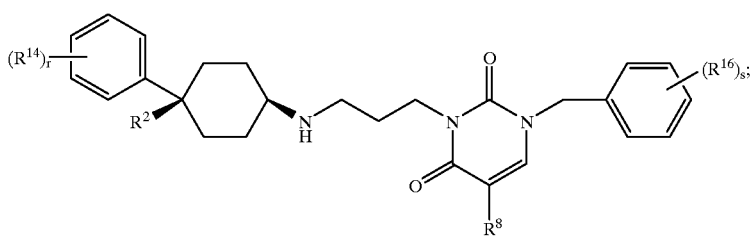

(IV)

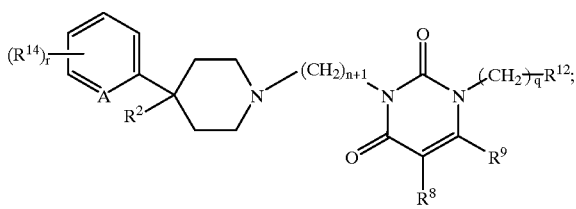

(V)

wherein A is C—$R^{14}$ or N;

$R^2$ is hydrogen, cyano, hydroxy, $CO_2R^c$, $C(=O)N(R^c)_2$, $NR^cC(=O)R^c$ or $NR^cSO_2R^c$;

$R^8$ and $R^9$ are each independently selected from hydrogen, halo, cyano, $C_1$-$C_4$ alkyl, $C_1$-$C_4$ alkoxy, fluorinated $C_1$-$C_4$ alkyl, fluorinated $C_1$-$C_4$ alkoxy, $CO_2R^c$, $C(=O)R^c$, $C(=O)N(R^c)_2$, phenyl, and mono- or di-substituted phenyl; wherein each substituent on the substituted phenyl is independently selected from fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ and $SO_2NH_2$;

$R^{12}$ is hydrogen, $C_1$-$C_4$ alkyl, $C_3$-$C_6$ cycloalkyl, $C_1$-$C_4$ alkoxy, fluorinated $C_1$-$C_4$ alkyl, fluorinated $C_1$-$C_4$ alkoxy, $CO_2R^c$, phenyl, or mono- or di-substituted phenyl; wherein each substituent on the substituted phenyl is independently selected from halo, nitro, cyano, hydroxy, amino, $C_1$-$C_4$ alkyl, $C_1$-$C_4$ alkoxy, fluorinated $C_1$-$C_4$ alkyl, fluorinated $C_1$-$C_4$ alkoxy, $CO_2R^c$, $C(=O)N(R^c)_2$ and $SO_2N(R^c)_2$;

each $R^{14}$ is independently hydrogen, halo, cyano, hydroxy, amino, $C_1$-$C_4$ alkyl, $C_1$-$C_4$ alkoxy, fluorinated $C_1$-$C_4$ alkyl, fluorinated $C_1$-$C_4$ alkoxy, $CO_2R^c$, $C(=O)N(R^c)_2$ or $SO_2N(R^c)_2$;

$R^c$ is hydrogen or $C_1$-$C_4$ alkyl; and n is an integer of from 1 to 3;

q is an integer of from 0 to 2; and r is an integer of from 0 to 2;

or a pharmaceutically acceptable salt thereof.

In a sub-class of the second class is a compound of Formula (V), wherein $R^{12}$ is of formula (VI):

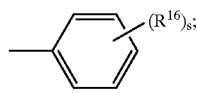

(VI)

wherein each $R^{16}$ is independently hydrogen, fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ or $SO_2NH_2$;

q is 1;

s is an integer of from 0 to 2;

and all other variables are as defined above for the second class;

or a pharmaceutically acceptable salt thereof.

Still other compounds exemplifying the invention include, but are not limited to, those selected from the group consisting of:

1-benzyl-3-{3-[4-(4-fluorophenyl)piperidin-1-yl]propyl}-5-methyl-1H-pyrimidine-2,4-dione;

1-[3-(3-benzyl-5-methyl-2,6-dioxo-3,6-dihydro-2H-pyrimidin-1-yl)propyl]-4-orthotolylpiperidine-4-carbonitrile;

2-{1-[3-(3-benzyl-5-methyl-2,6-dioxo-3,6-dihydro-2H-pyrimidin-1-yl)propyl]piperidin-4-yl}benzonitrile; and pharmaceutically acceptable salts thereof.

In a third class of the present invention is a compound of Formula (VII):

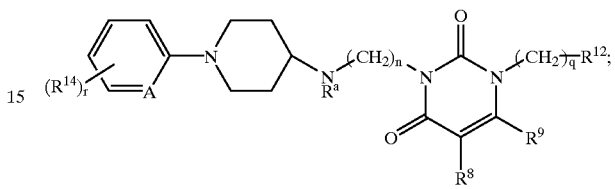

(VII)

wherein A is C—$R^{14}$ or N;

$R^8$ and $R^9$ are each independently selected from hydrogen, halo, cyano, $C_1$-$C_4$ alkyl, $C_1$-$C_4$ alkoxy, fluorinated $C_1$-$C_4$ alkyl, fluorinated $C_1$-$C_4$ alkoxy, $CO_2R^c$, $C(=O)R^c$, $C(=O)N(R^c)_2$, phenyl, and mono- or di-substituted phenyl; wherein each substituent on the substituted phenyl is independently selected from fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ and $SO_2NH_2$;

$R^{12}$ is hydrogen, $C_1$-$C_4$ alkyl, $C_3$-$C_6$ cycloalkyl, $C_1$-$C_4$ alkoxy, fluorinated $C_1$-$C_4$ alkyl, fluorinated $C_1$-$C_4$ alkoxy, phenyl, or mono- or di-substituted phenyl; wherein each substituent on the substituted phenyl is independently selected from halo, nitro, cyano, hydroxy, amino, $C_1$-$C_4$ alkyl, $C_1$-$C_4$ alkoxy, fluorinated $C_1$-$C_4$ alkyl, fluorinated $C_1$-$C_4$ alkoxy, $CO_2R^c$, $C(=O)N(R^c)_2$ and $SO_2N(R^c)_2$;

each $R^{14}$ is independently hydrogen, halo, cyano, hydroxy, amino, $C_1$-$C_4$ alkyl, $C_1$-$C_4$ alkoxy, fluorinated $C_1$-$C_4$ alkyl, fluorinated $C_1$-$C_4$ alkoxy, $CO_2R^c$, $C(=O)N(R^c)_2$ or $SO_2N(R^c)_2$;

$R^a$ is hydrogen or $C_1$-$C_6$ alkyl;

$R^c$ is hydrogen or $C_1$-$C_4$ alkyl; and n is an integer of from 2 to 4;

q is an integer of from 0 to 2; and r is an integer of from 0 to 2;

or a pharmaceutically acceptable salt thereof

Still another compound exemplifying the invention is 3-{3-[1-(4-fluoro-2-methoxyphenyl)piperidin-4-ylamino]propyl}-5-methyl-1H-pyrimidine-2,4-dione; or a pharmaceutically acceptable salt thereof In a sub-class of the third class is a compound of Formula (VII), wherein $R^{12}$ is of formula (VI):

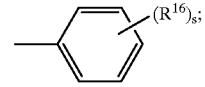

(VI)

wherein each $R^{16}$ is independently hydrogen, fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ or $SO_2NH_2$;

q is 1;

s is an integer of from 0 to 2;

and all other variables are as defined above for the third class;

or a pharmaceutically acceptable salt thereof.

In a fourth class of the present invention is a compound of Formula (VIII):

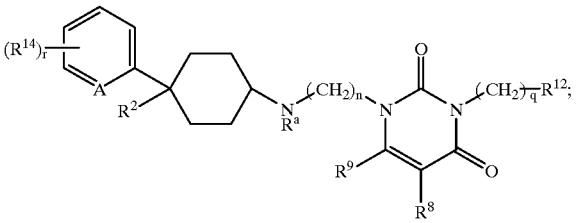

(VIII)

wherein A is $C-R^{14}$ or N;

$R^2$ is hydrogen, cyano, hydroxy, $CO_2R^c$, $C(=O)N(R^c)_2$, $NR^cC(=O)R^c$ or $NR^cSO_2R^c$;

$R^8$ and $R^9$ are each independently selected from hydrogen, halo, cyano, $C_1-C_4$ alkyl, $C_1-C_4$ alkoxy, fluorinated $C_1-C_4$ alkyl, fluorinated $C_1-C_4$ alkoxy, $CO_2R^c$, $C(=O)R^c$, $C(=O)N(R^c)_2$, phenyl, and mono- or di-substituted phenyl; wherein each substituent on the substituted phenyl is independently selected from fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ and $SO_2NH_2$;

$R^{12}$ is hydrogen, $C_1-C_4$ alkyl, $C_3-C_6$ cycloalkyl, $C_1-C_4$ alkoxy, fluorinated $C_1-C_4$ alkyl, fluorinated $C_1-C_4$ alkoxy, $CO_2R^c$, phenyl, or mono- or di-substituted phenyl; wherein each substituent on the substituted phenyl is independently selected from halo, nitro, cyano, hydroxy, amino, $C_1-C_4$ alkyl, $C_1-C_4$ alkoxy, fluorinated $C_1-C_4$ alkyl, fluorinated $C_1-C_4$ alkoxy, $CO_2R^c$, $C(=O)N(R^c)_2$ and $SO_2N(R^c)_2$;

each $R^{14}$ is independently hydrogen, halo, cyano, hydroxy, amino, $C_1-C_4$ alkyl, $C_1-C_4$ alkoxy, fluorinated $C_1-C_4$ alkyl, fluorinated $C_1-C_4$ alkoxy, $CO_2R^c$, $C(=O)N(R^c)_2$ or $SO_2N(R^c)_2$;

$R^a$ is hydrogen or $C_1-C_6$ alkyl;

$R^c$ is hydrogen or $C_1-C_4$ alkyl; and n is an integer of from 2 to 4;

q is an integer of from 0 to 2; and r is an integer of from 0 to 2;

or a pharmaceutically acceptable salt thereof.

In a sub-class of the fourth class is a compound of Formula (VIII), wherein $R^{12}$ is of formula (VI):

(VI)

wherein each $R^{16}$ is independently hydrogen, fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ or $SO_2NH_2$;

q is 1;

s is an integer of from 0 to 2;

and all other variables are as defined above for the fourth class;

or a pharmaceutically acceptable salt thereof.

Still other compounds exemplifying the present invention are those selected from the group consisting of:

cis-2-{4-[3-(3-benzyl-5-methyl-2,4-dioxo-3,4-dihydro-2H-pyrimidin-1-yl)propylamino]-1-cyanocyclohexyl}benzonitrile;

trans-2-{4-[3-(3-benzyl-5-methyl-2,4-dioxo-3,4-dihydro-2H-pyrimidin-1-yl)propylamino]-1-cyanocyclohexyl}benzonitrile; and pharmaceutically acceptable salts thereof.

The present invention also includes a pharmaceutical composition comprising a therapeutically effective amount of any of the compounds described above and a pharmaceutically acceptable carrier. In one embodiment is a pharmaceutical composition made by combining any of the compounds described above and a pharmaceutically acceptable carrier. The present invention further includes a process for making a pharmaceutical composition comprising combining any of the compounds described above and a pharmaceutically acceptable carrier.

The present invention further includes a pharmaceutical composition as described in the preceding paragraph further comprising a therapeutically effective amount of a testosterone 5-alpha reductase inhibitor. In one embodiment, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor), or a dual type 1 and type 2 testosterone 5-alpha reductase inhibitor. In another embodiment, the testosterone 5-alpha reductase inhibitor is a type 2 testosterone 5-alpha reductase inhibitor. The testosterone 5-alpha reductase inhibitor is suitably finasteride.

The present invention also includes a method of treating benign prostatic hyperplasia in a subject in need thereof which comprises administering to the subject a therapeutically effective amount of any of the compounds (or any of the compositions) described above. In one embodiment of the method of treating BPH, the compound (or composition) does not cause a fall in blood pressure at dosages effective to alleviate BPH. In another embodiment of the method of treating BPH, the compound is administered in combination with a testosterone 5-alpha reductase inhibitor. A suitable testosterone 5-alpha reductase inhibitor for use in the method is finasteride.

The present invention also includes a method of inhibiting contraction of prostate tissue or relaxing lower urinary tract tissue in a subject in need thereof which comprises administering to the subject a therapeutically effective amount of any of the compounds (or any of the compositions) described above. In one embodiment of the method of inhibiting contraction of prostate tissue or relaxing lower urinary tract tissue, the compound (or composition) additionally does not cause a fall in blood pressure at dosages effective to inhibit contraction of prostate tissue. In another embodiment, the compound is administered in combination with a testosterone 5-alpha reductase inhibitor; the testosterone 5-alpha reductase inhibitor is suitably finasteride.

The present invention also includes a method of treating a disease which is susceptible to treatment by antagonism of the alpha 1a receptor which comprises administering to a subject in need thereof an amount of any of the compounds described above effective to treat the disease. Diseases which are susceptible to treatment by antagonism of the alpha 1a receptor include, but are not limited to, BPH, high intraocular pressure, high cholesterol, impotency, sympathetically mediated pain, migraine (see Vatz, *Headache* (1997), 37: 107–108) and cardiac arrhythmia.

The present invention also includes the use of any of the compounds described above in the preparation of a medicament for: a) treating benign prostatic hyperplasia; b) relaxing lower urinary tract tissue; or c) inhibiting contraction of prostate tissue; in a subject in need thereof.

The present invention further includes the use of any of the alpha 1a antagonist compounds described above and a 5-alpha reductase inhibitor for the manufacture of a medicament for: a) treating benign prostatic hyperplasia; b) relaxing lower urinary tract tissue; or c) inhibiting contraction of prostate tissue which comprises an effective amount of the alpha 1a antagonist compound and an effective amount of 5-alpha reductase inhibitor, together or separately.

As used herein, the term "$C_1$–$C_6$ alkyl" means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_1$–$C_4$ alkyl" means n-, iso-, sec- and t-butyl, n- and isopropyl, ethyl and methyl.

The term "$C_1$–$C_6$ alkoxy" means an —O-alkyl group wherein alkyl is $C_1$ to $C_6$ alkyl. "$C_1$–$C_4$ alkoxy" has an analogous meaning; i.e., it is an alkoxy group selected from methoxy, ethoxy, n-propoxy, isopropoxy, n-butoxy, isobutoxy, tertbutoxy, and sec-butoxy.

The term "$C_3$–$C_8$ cycloalkyl" means a cyclic ring of an alkane having three to eight total carbon atoms (i.e., cyclopropyl, cyclobutyl, cyclopentyl, cyclohexyl, cycloheptyl or cyclooctyl). "$C_3$–$C_6$ cycloalkyl" refers to a cyclic ring selected from cyclopropyl, cyclobutyl, cyclopentyl, and cyclohexyl.

The term "halo" (which may alternatively be referred to as "halogen") refers to fluoro, chloro, bromo, and iodo (alternatively fluorine, chlorine, bromine and iodine).

The term "fluorinated $C_1$–$C_6$ alkyl" (which may alternatively be referred to as "$C_1$–$C_6$ fluoroalkyl") means a $C_1$ to $C_6$ linear or branched alkyl group as defined above with one or more fluorine substituents. The term "fluorinated $C_1$–$C_4$ alkyl" has an analogous meaning. Representative examples of suitable fluoroalkyls include the series $CH_2)_{0-4}CF_3$ (i.e., trifluoromethyl, 2,2,2-trifluoroethyl, 3,3,3-trifluoro-n-propyl, etc.), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "fluorinated $C_3$–$C_8$ cycloalkyl" (which may alternatively be referred to as "$C_3$–$C_8$ fluorocycloalkyl") means a cycloalkyl group as defined above with one or more fluorine substituents. "Fluorinated $C_3$–$C_6$ cycloalkyl" has an analogous meaning. Representative examples of suitable fluorocycloalkyls include all isomers of fluorocyclohexyl (i.e., 1-, 2-, 3-, and 4-fluorocyclohexyl), difluorocyclohexyl (e.g., 2,4-difluorocyclohexyl, 3,4-difluorocyclohexyl, etc.), fluorocyclopentyl, and so forth.

The term "fluorinated $C_1$–$C_6$ alkoxy" (which may alternatively be referred to as "$C_1$–$C_6$ fluoroalkoxy") means a $C_1$–$C_6$ alkoxy group as defined above wherein the alkyl moiety has one or more fluorine substituents. "Fluorinated $C_1$–$C_4$ alkoxy" has an analogous meaning. Representative examples include the series $O(CH_2)_{0-4}CF_3$ (i.e., trifluoromethoxy, 2,2,2-trifluoroethoxy, 3,3,3-trifluoro-n-propoxy, etc.), 1,1,1,3,3,3-hexafluoroisopropoxy, and so forth.

The term "heterocyclic" (which may alternatively be referred to as "heterocycle") refers to a stable 5- to 7-membered monocyclic ring system which may be saturated or unsaturated, and which consists of carbon atoms and from one to three heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Suitable heterocyclics include pyridyl, thienyl,

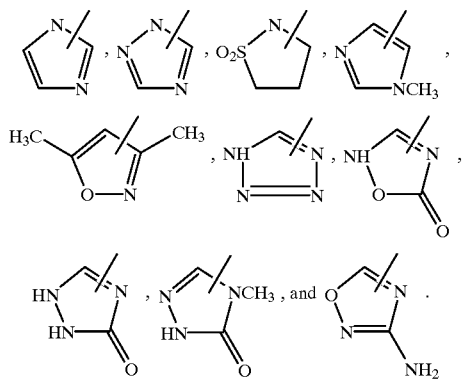

The term "thienyl," as used herein, refers to the group

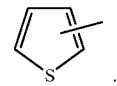

The term "aryl" refers to phenyl, substituted phenyl, naphthyl, and substituted naphthyl.

The term "heteroaryl" refers to heterocyclic or substituted heterocyclic.

The term "substituted" includes mono- and poly-substitution by a named substituent to the extent such single and multiple substitution is chemically allowed.

The term "poly-substituted" refers herein to multiple degrees of substitution by a named substituent or substituents. For example, the term "poly-substituted phenyl" denotes di-, tri-, tetra- and penta-substitution by a named substituent or a combination of named substituents (e.g., "di-substituted phenyl wherein each substituent is independently selected from fluoro, methoxy and cyano" represents such moieties as 2,4-difluorophenyl, 3,4-difluorophenyl, 2-methoxy-4-fluorophenyl, 2-fluoro4-cyanophenyl, 2-cyano4-fluorophenyl, 3-cyano-4-fluorophenyl, etc.)

It is understood that the definition of a substituent (e.g., $CO_2R^c$) or variable (e.g., $R^c$) at a particular location in a molecule is independent of its definitions at other locations in that molecule. Thus, for example, when $R^1$ is mono-substituted phenyl wherein the substituent is $CO_2R^c=CO_2H$, and $R^{12}$ is also mono-substituted phenyl wherein the substituent is $CO_2R^c$, it is understood that the substituent on the phenyl in $R^{12}$ can be any one of $CO_2H$, $CO_2Me$, $CH_2Et$, $CO_2Pr$, $CH_2CO_2H$, $CH_2CO_2Me$, $CH_2CO_2Et$, $CH_2CO_2Pr$, $CH_2)_2CO_2H$, etc. As another example, $NR^cC(=O)R^c$ represents $NHC(=O)H$, $NHC(=O)Me$, $NMeC(=O)Me$, $NMeC(=O)Et$, etc. As still another example,

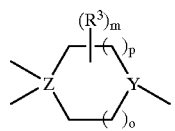

wherein m=2, o=1, and p=1, represents moieties such as

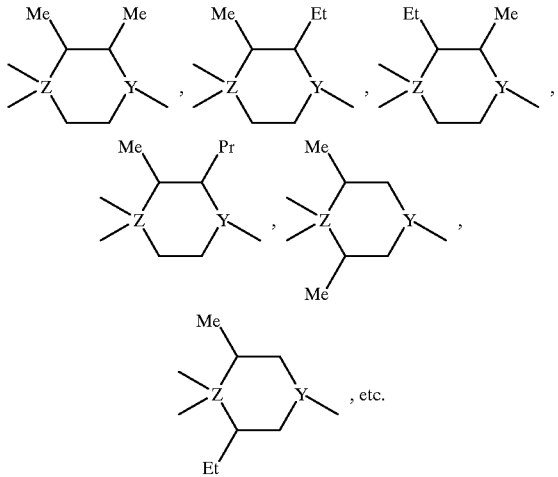

It is also understood that the definition of a substituent or variable at a particular location in a molecule is independent of the definition of another occurrence of the same substituent or variable at the same location. Thus, $C(=O)N(R^c)_2$ represents groups such as —$C(=O)NH_2$, —$C(=O)NHCH_3$, —$C(=O)NHC_2H_5$, —$C(=O)N(CH_3)C_2H_5$, etc.

It is understood that substituents and substitution patterns on the compounds of the instant invention can be selected by one of ordinary skill in the art to provide compounds that are chemically stable and that can be readily synthesized by the methods set forth below and, when viewed in the light of this disclosure, by techniques known in the art. Where multiple substituent moieties are disclosed or claimed, the substituted compound can be independently substituted by one or more of the disclosed or claimed substituent moieties, singly or plurally.

Other embodiments for the variables and substituents set forth in Formula (I) include the following:

$R^1$ is phenyl, mono- or di- or tri-substituted phenyl, pyridyl, mono- or di-substituted pyridyl, thienyl, or mono-substituted thienyl; or is phenyl, mono- or di- or tri-substituted phenyl, or pyridyl; or is phenyl, or mono- or di-substituted phenyl.

When $R^1$ is substituted phenyl, each substituent is independently selected from halo, nitro, cyano, hydroxy, amino, $C_1$–$C_4$ alkyl, $C_3$–$C_6$ cycloalkyl, $C_1$–$C_4$ alkoxy, fluorinated $C_1$–$C_4$ alkyl, fluorinated $C_3$–$C_6$ cycloalkyl, fluorinated $C_1$–$C_4$ alkoxy, $CO_2R^c$, $C(=O)N(R^c)_2$ and $SO_2N(R^c)_2$; or is independently selected from fluoro, chloro, nitro, cyano, hydroxy, amino, methyl, ethyl, methoxy, ethoxy, trifluoromethyl, trifluoromethoxy, trifluoroethoxy, $CO_2CH_3$, $C(=O)NH_2$ and $SO_2NH_2$.

When $R^1$ is substituted pyridyl, each substituent is independently selected from halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$; or is independently selected from fluoro, chloro, nitro, cyano, hydroxy, amino, methyl, ethyl, methoxy, ethoxy, trifluoromethyl, trifluoromethoxy, trifluoroethoxy, $CO_2CH_3$, $C(=O)NH_2$ and $SO_2NH_2$.

When $R^1$ is substituted thienyl, each substituent is independently selected from halo and $C_1$–$C_4$ alkyl; or is independently selected from fluoro, chloro, methyl and ethyl.

In still another embodiment, $R^1$ is of formula

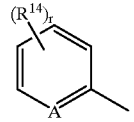

wherein A is C—$R^{14}$ or N; each $R^{14}$ is independently hydrogen, halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ or $SO_2N(R^c)_2$; and r is an integer of from 0 to 2. In one aspect, A is C—$R^{14}$ (e.g., CH).

$R^2$ is hydrogen, cyano, $CO_2R^c$, $C(=O)N(R^c)_2$, $NR^cC(=O)R^c$, $NR^cSO_2R^c$, phenyl, mono- or di- or tri-substituted phenyl, pyridyl, mono- or di-substituted pyridyl, thienyl, or mono-substituted thienyl; or is hydrogen, cyano, $CO_2R^c$, $C(=O)N(R^c)_2$, $NR^cC(=O)R^c$, $NR^cSO_2R^c$, phenyl, mono- or di- or tri-substituted phenyl, or pyridyl. In other embodiments, $R^2$ is hydrogen, cyano, $CO_2R^c$, $C(=O)N(R^c)_2$, $NR^cC(=O)R^c$, $NR^cSO_2R^c$, phenyl, mono- or di-substituted phenyl, or pyridyl; or is hydrogen, cyano, $CO_2R^c$, $C(=O)N(R^c)_2$, $NR^cC(=O)R^c$ or $NR^cSO_2R^c$; or is hydrogen, cyano, $CO_2CH_3$, $C(=O)NH_2$ or $SO_2NH_2$.

When $R^2$ is substituted phenyl, each substituent is independently selected from halo, nitro, cyano, hydroxy, amino, $C_1$–$C_4$ alkyl, $C_3$–$C_6$ cycloalkyl, $C_1$–$C_4$ alkoxy, fluorinated $C_1$–$C_4$ alkyl, fluorinated $C_3$–$C_6$ cycloalkyl, fluorinated $C_1$–$C_4$ alkoxy, $CO_2R^c$, $C(=O)N(R^c)_2$ and $SO_2N(R^c)_2$; or is independently selected from fluoro, chloro, nitro, cyano, hydroxy, amino, methyl, ethyl, methoxy, ethoxy, trifluoromethyl, trifluoromethoxy, trifluoroethoxy, $CO_2CH_3$, $C(=O)NH_2$ and $SO_2NH_2$.

When $R^2$ is substituted pyridyl, each substituent is independently selected from halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$; or is independently selected from fluoro, chloro, nitro, cyano, hydroxy, amino, methyl, ethyl, methoxy, ethoxy, trifluoromethyl, trifluoromethoxy, trifluoroethoxy, $CO_2CH_3$, $C(=O)NH_2$ and $S_2NH_2$.

When $R^2$ is substituted thienyl, each substituent is independently selected from halo and $C_1$–$C_4$ alkyl; or is independently selected from fluoro, chloro, methyl and ethyl.

Each $R^3$ is methyl or ethyl.

$R^4$, $R^5$, $R^{10}$ and $R^{11}$ are each independently selected from hydrogen and $C_1$–$C_6$ alkyl; or are each independently selected from hydrogen and $C_1$–$C_4$ alkyl; or are each independently selected from hydrogen, methyl and ethyl. In still other embodiments, $R^4$ and $R^5$ are either both hydrogen, or one of $R^4$ and $R^5$ is hydrogen and the other is hydrogen or $C_1$–$C_6$ alkyl. In one aspect of the preceding embodiment, $R^4$ and $R^5$ are both hydrogen. Similarly, $R^{10}$ and $R^{11}$ are either both hydrogen, or one of $R^{10}$ and $R^{11}$ is hydrogen and the other is hydrogen or $C_1$–$C_6$ alkyl. In one aspect of the preceding embodiment, $R^{10}$ and $R^{11}$ are both hydrogen.

$R^6$ and $R^7$ are each independently selected from hydrogen, $C_1$–$C_4$ alkyl, and fluorinated $C_1$–$C_4$ alkyl; or $R^6$ and $R^7$ are taken together to form oxo. In one aspect of the preceding embodiment, $R^6$ and $R^7$ are taken together to form oxo.

$R^8$ and $R^9$ are each independently selected from hydrogen, halo, cyano, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, $C(=O)R^c$, $C(=O)N(R^c)_2$, phenyl, mono- or di-substituted phenyl, pyridyl, mono- or di-substituted pyridyl, thienyl and mono-substituted thienyl; or are each independently selected from hydrogen, halo, cyano, $C_1$–$C_4$ alkyl, $C_3$–$C_6$ cycloalkyl, $C_1$–$C_4$ alkoxy, fluorinated $C_1$–$C_4$ alkyl, fluorinated $C_3$–$C_6$ cycloalkyl, fluorinated $C_1$–$C_4$ alkoxy, $CO_2R^c$, $C(=O)R^c$, $C(=O)N(R^c)_2$, phenyl, mono- or di-substituted phenyl, pyridyl, mono- or di-substituted pyridyl, thienyl and mono-substituted thienyl. In still other embodiments, $R^8$ and $R^9$ are each independently selected from hydrogen, halo, cyano, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)R^c$, $C(=O)N(R^c)_2$, phenyl, mono- or di-substituted phenyl, and pyridyl; or are each independently selected from hydrogen, halo, cyano, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)R^c$, $C(=O)N(R^c)_2$, phenyl and mono- or di-substituted phenyl.

When one or both of $R^8$ and $R^9$ is substituted phenyl, each substituent is independently selected from halo, nitro, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$; or is independently selected from fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ and $SO_2NH_2$.

When one or both of $R^8$ and $R^9$ is substituted pyridyl, each substituent is independently selected from halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$; or is independently selected from fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ and $SO_2NH_2$.

When one or both of $R^8$ and $R^9$ is substituted thienyl, each substituent is independently selected from halo and $C_1$–$C_4$ alkyl; or is independently selected from fluoro, chloro, methyl and ethyl.

$R^{12}$ is hydrogen, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, phenyl, mono- or di-substituted phenyl, pyridyl, mono- or di-substituted pyridyl, thienyl, mono-substituted thienyl,

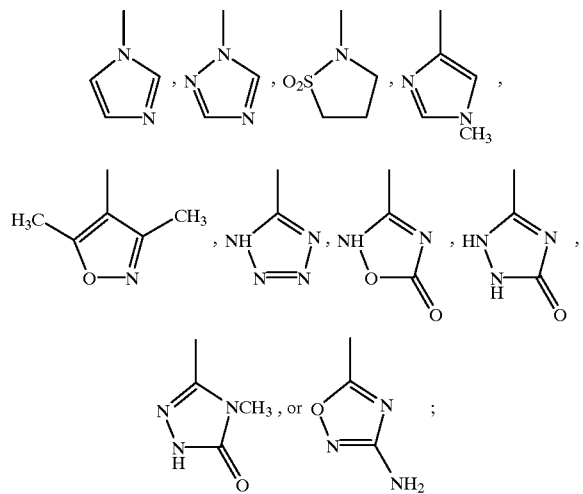

or is hydrogen, $C_1$–$C_4$ alkyl, $C_3$–$C_6$ cycloalkyl, $C_1$–$C_4$ alkoxy, fluorinated $C_1$–$C_4$ alkyl, fluorinated $C_3$–$C_6$ cycloalkyl, fluorinated $C_1$–$C_4$ alkoxy, $CO_2R^c$, phenyl, mono- or di-substituted phenyl, pyridyl, mono- or di-substituted pyridyl, thienyl, or mono-substituted thienyl. In still other embodiments, $R^{12}$ is hydrogen, $C_1$–$C_4$ alkyl, $C_3$–$C_6$ cycloalkyl, $C_1$–$C_4$ alkoxy, fluorinated $C_1$–$C_4$ alkyl, fluorinated $C_1$–$C_4$ alkoxy, $CO_2R^c$, phenyl, mono- or di-substituted phenyl, or pyridyl; or is hydrogen, $C_1$–$C_4$ alkyl, $C_3$–$C_6$ cycloalkyl, $C_1$–$C_4$ alkoxy, fluorinated $C_1$–$C_4$ alkyl, fluorinated $C_1$–$C_4$ alkoxy, $CO_2R^c$, phenyl, or mono- or di-substituted phenyl.

When $R^{12}$ is substituted phenyl, each substituent on the substituted phenyl is independently selected from halo, nitro, cyano, hydroxy, amino, $C_1$–$C_4$ alkyl, $C_3$–$C_6$ cycloalkyl, $C_1$–$C_4$ alkoxy, fluorinated $C_1$–$C_4$ alkyl, fluorinated $C_3$–$C_6$ cycloalkyl, fluorinated $C_1$–$C_4$ alkoxy, $CO_2R^c$, $C(=O)N(R^c)_2$ and $SO_2N(R^c)_2$; or is independently selected from halo, nitro, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$; or is independently selected from fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ and $SO_2NH_2$.

When $R^{12}$ is substituted pyridyl, each substituent on the pyridyl is independently selected from halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$; or is independently selected from fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ and $SO_2NH_2$.

When $R^{12}$ is substituted thienyl, each substituent on the thienyl is independently selected from halo and $C_1$–$C_4$ alkyl.

In one embodiment, $R^{12}$ is of formula:

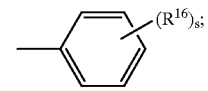

wherein each $R^{16}$ is independently hydrogen, fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ or $SO_2NH_2$; and s is an integer of from 0 to 2.

$R^a$ and $R^b$ are each independently selected from hydrogen, $C_1$–$C_6$ alkyl, and $C_3$–$C_6$ cycloalkyl; or are each independently selected from hydrogen and $C_1$–$C_4$ alkyl; or are each hydrogen (i.e., X is $CH_2$ or NH).

$R^c$ is hydrogen or $C_1$–$C_4$ alkyl; or is hydrogen, methyl or ethyl.

m is 0 to 2; or is 0 or 1; or is 0.

When X is $NR^a$, n is preferably 2 or 3; or is 3. When X is $CR^aR^b$, n is preferably 1 or 2; or is 2.

o and p are selected such that the sum of o+p is 1 or 2; or are selected such that the sum of o+p is 2.

q is 1.

Representative compounds of the present invention exhibit selectivity for the human alpha 1a adrenergic receptor. One implication of this selectivity is that these compounds display selectivity for lowering intraurethral pressure without substantially affecting diastolic blood pressure.

Representative compounds of this invention display sub-micromolar affinity for the human alpha 1a adrenergic receptor subtype while displaying lower affinity for the human alpha 1d and alpha 1b adrenergic receptor subtypes, and many other G-protein coupled human receptors. Particular representative compounds of this invention exhibit nanomolar and subnanomolar affinity for the human alpha 1a adrenergic receptor subtype while displaying at least about 10 fold lower affinity for the human alpha 1d and alpha 1b adrenergic receptor subtypes, and many other G-protein coupled human receptors (e.g., serotonin, dopamine, alpha 2 adrenergic, beta adrenergic or muscarinic receptors). Still other compounds of this invention exhibit nanomolar and subnanomolar affinity for the human alpha 1a adrenergic receptor subtype while displaying at least about 20 fold lower affinity for the human alpha 1d and alpha 1b adrenergic receptor subtypes, in addition to exhibiting selectivity over other G-protein coupled human receptors (e.g., serotonin, dopamine, alpha 2 adrenergic, beta adrenergic or muscarinic receptors).

These compounds are administered in dosages effective to antagonize the alpha 1a receptor where such treatment is needed; e.g., treatment of BPH. For use in medicine, the salts of the compounds of this invention refer to non-toxic "pharmaceutically acceptable salts." Other salts may, however, be useful in the preparation of the compounds according to the invention or in the prepartion of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

Acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, n-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Compounds of this invention are used to reduce the acute symptoms of BPH. Thus, compounds of this invention may be used alone or in combination with more long-term anti-BPH therapeutics, such as testosterone 5-a reductase inhibitors, including PROSCAR® (finasteride). Aside from their utility as anti-BPH agents, these compounds may be used to induce highly tissue-specific, localized alpha 1a adrenergic receptor blockade whenever this is desired. Effects of this blockade include reduction of intra-ocular pressure, control of cardiac arrhythmias, and possibly a host of alpha 1a receptor mediated central nervous system events.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient Conventional procedures for the selection and preparation of suitable prodrug derivatives are described, for example, in Design of Prodrugs, ed. H. Bundgaard, Elsevier, 1985. Metabolites of these compounds include active species produced upon introduction of compounds of this invention into the biological milieu.

Where the compounds according to the invention have at least one chiral center, they may accordingly exist as enantiomers. Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also encompassed within the scope of this invention.

The term "selective alpha 1a adrenergic receptor antagonist," as used herein, refers to an alpha 1a antagonist compound which is at least about-ten fold selective for the human alpha 1a adrenergic receptor as compared to the human alpha 1b, alpha 1d, alpha 2a, alpha 2b and alpha 2c adrenergic receptors.

The term "lower urinary tract tissue," as used herein, refers to and includes, but is not limited to, prostatic smooth muscle, the prostatic capsule, the urethra and the bladder neck.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The present invention includes pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, the term "composition" encompasses a product comprising the specified ingredients in the specified amounts, as well as any product which results, directly or indirectly, from combination of the specified ingredients in the specified amounts.

The liquid forms in which the novel compositions of the present invention may be incorporated for administration orally or by injection include aqueous solutions, suitably flavoured syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known in the art.

The specificity of binding of compounds showing affinity for the alpha 1a receptor is shown by comparing affinity to membranes obtained from transfected cell lines that express the alpha 1a receptor and membranes from cell lines or tissues known to express other types of alpha (e.g., alpha 1d, alpha 1b) or beta adrenergic receptors. Expression of the cloned human alpha 1d, alpha 1b, and alpha 1a receptors and comparison of their binding properties with known selective antagonists provides a rational way for selection of compounds and discovery of new compounds with predictable pharmacological activities. Antagonism by these compounds of the human alpha 1a adrenergic receptor subtype may be functionally demonstrated in anesthetized animals. These compounds may be used to increase urine flow without exhibiting hypotensive effects.

The ability of compounds of the present invention to specifically bind to the alpha 1a receptor makes them useful for the treatment of BPH. The specificity of binding of compounds showing affinity for the alpha 1a receptor is compared against the binding affinities to other types of alpha or beta adrenergic receptors. The human alpha adrenergic receptor of the 1a subtype was recently identified, cloned and expressed as described in PCT International Application Publication Nos. WO 94/08040, published Apr. 14, 1994 and WO 94/21660, published Sep. 29, 1994. The cloned human alpha 1a receptor, when expressed in mammalian cell lines, is used to discover ligands that bind to the receptor and alter its function. Expression of the cloned human alpha 1d, alpha 1b, and alpha 1a receptors and comparison of their binding properties with known selective antagonists provides a rational way for selection of compounds and discovery of new compounds with predictable pharmacological activities.

Compounds of this invention exhibiting human alpha 1a adrenergic receptor antagonism may further be defined by counterscreening. This is accomplished according to methods known in the art using other receptors responsible for mediating diverse biological functions. [See e.g., PCT International Application Publication No. WO 94/10989, published May 26, 1994; U.S. Pat. No. 5,403,847, issued Apr. 4, 1995]. Compounds which are both selective amongst the various human alpha1 adrenergic receptor subtypes and which have low affinity for other receptors, such as the alpha 2 adrenergic receptors, the β-adrenergic receptors, the muscarinic receptors, the serotonin receptors, the histamine receptors, and others are particularly preferred. The absence of these non-specific activities may be confirmed by using cloned and expressed receptors in an analogous fashion to the method disclosed herein for identifying compounds which have high affinity for the various human alpha1 adrenergic receptors. Furthermore, functional biological tests are used to confirm the effects of identified compounds as alpha 1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha 1a adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1a antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacrylamidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Compounds of this invention may be administered in any of the foregoing compositions and according to dosage regimens established in the art whenever specific blockade of the human alpha 1a adrenergic receptor is required.

The daily dosage of the products may be varied over a wide range; e.g., from about 0.01 to about 1000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams ofthe active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 20 mg/kg of body weight per day. Preferably, the range is from about 0.001 to about 10 mg/kg of body weight per day, and especially from about 0.001 mg/kg to about 7 mg/kg of body weight per day. The compounds may be administered on a regimen of 1 to 4 times per day.

Compounds of this patent disclosure may be used alone at appropriate dosages defined by routine testing in order to obtain optimal antagonism of the human alpha 1a adrenergic receptor while minimizing any potential toxicity. In addition, co-administration or sequential administration of other agents which alleviate the effects of BPH is desirable. Thus, in one embodiment, this invention is administration of compounds of this invention and a human testosterone 5-a reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. Nos. 4,377,584 and 4,760,071, for example). In addition to PROSCAR®, which is principally active in prostatic tissue due to its selectivity for human 5-a reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5a-reductase inhibitors have been described in WO 93/23420, EP 0572166; WO 93/23050; WO 93/23038; WO 93/23048; WO 93/23041; WO 93/23040; WO 93/23039; WO 93/23376; WO 93/23419, EP 0572165; WO 93/23051.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one embodiment of the present invention, a method of treating BPH is provided which comprises administering to a subject in need of treatment any of the compounds of the present invention in combination with finasteride effective to treat BPH. The dosage of finasteride administered to the subject is from about 0.01 mg per subject per day to about 50 mg per subject per day in combination with an alpha 1a antagonist. In one aspect, the dosage of finasteride in the combination is from about 0.2 mg per subject per day to about 10 mg per subject per day, and, in another aspect, from about 1 to about 7 mg per subject to day (e.g., about 5 mg per subject per day).

For the treatment of benign prostatic hyperplasia, compounds of this invention exhibiting alpha 1a adrenergic receptor blockade can be combined with a therapeutically effective amount of a 5a-reductase 2 inhibitor, such as finasteride, in addition to a 5a-reductase 1 inhibitor, such as 4,7β-dimethyl-4-aza-5a-cholestan-3-one, in a single oral, systemic, or parenteral pharmaceutical dosage formulation. Alternatively, a combined therapy can be employed wherein the alpha 1a adrenergic receptor antagonist and the 5a-reductase 1 or 2 inhibitor are administered in separate oral, systemic, or parenteral dosage formulations. See, e.g., U.S. Pat. No. 4,377,584 and U.S. Pat. No. 4,760,071 which describe dosages and formulations for 5a-reductase inhibitors.

Abbreviations used in the instant specification, particularly the Schemes and Examples, are as follows:

Boc or BOC=t-butyloxycarbonyl
Bu=butyl
DMF=N,N-dimethylformamide
DMSO=dimethylsulfoxide
EDTA=ethylenediamine tetraacetic acid
Et=ethyl
FAB MS=fast atom bombardment mass spectroscopy
M.P.=melting point
NMR=nuclear magnetic resonance
Ph=phenyl
Pr=propyl
THF=tetrahydrofuran The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Many of the compounds claimed within this invention can be prepared via Schemes 1–6 shown below. Scheme 1 describes the preparation of piperidinyl-containing pyrimidinedione compounds of the present invention. Pyrimidinedione precursor 1 can be alkylated at N1 with a suitable alkylating agent such as a halide to form 2. The alkylated pyrimidinedione 2 can then be dissolved in a polar, aprotic solvent such as DMF, and to the resulting solution is added tetrabutylammonium bromide and an inorganic base (e.g., NaOH). The resulting suspension is maintained at elevated temperature (e.g., about 60 C) and then cooled to about ambient temperature, after which a dibromide (e.g., 1,3-dibromopropane) is added, and the resulting reaction mixture returned to elevated temperature (e.g., about 50 C) to provide 3. To bromide compound 3 and piperidine 4 (e.g., a 4-aryl- or 4-heteroarylpiperidine) suspended in an aprotic solvent such as acetonitrile is added an inorganic base (e.g., potassium carbonate) and an inorganic iodide source (e.g., NaI), and the resulting reaction mixture is refluxed to provide 5.

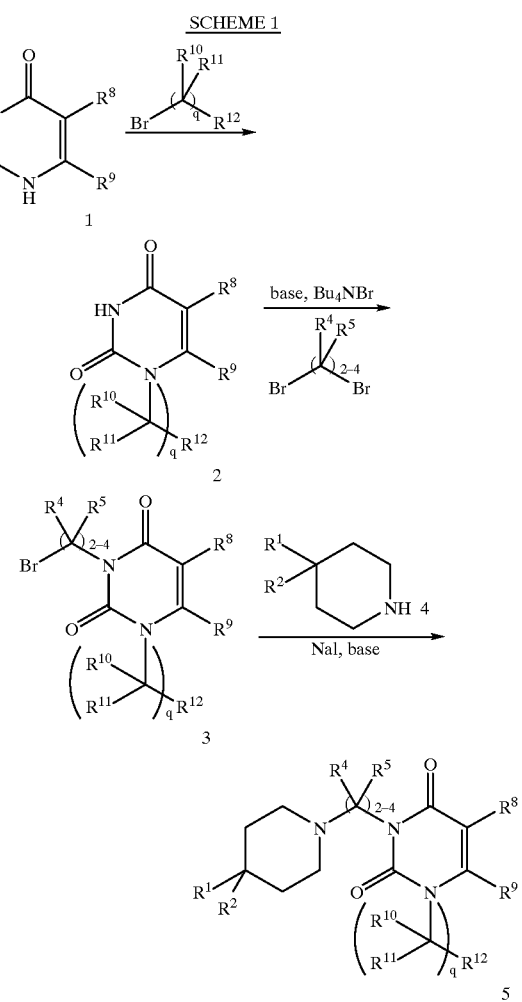

SCHEME 1

Scheme 2 describes the preparation of aminocyclohexyl and aminopiperidinyl pyrimidinedione compounds of the invention. The N1,N3-dialkylated pyrimidinedione intermediate 6 is formed from 2 using the methodology described in Scheme 1, except that a Boc-protected bromoalkylamine is employed instead of a dibromide. The alkyl nitrogen is liberated by treatment of 6 with an acid such as HCl or trifluoroacetic acid, at or below ambient temperature to provide 7. Amine 7 and a ketone 8 (e.g., a 4-aryl- or 4-heteroaryl-4-cyanocyclohexanone or an N-aryl- or N-heteroaryl-4-piperidone) are combined in an ether such as THF. When the amine is formulated as a salt, an organic base (e.g., triethylamine or N,N-diisoproplethylamine) is usually added as well. A Lewis acid (e.g., titanium tetraisopropoxide) is then added, and the resulting reaction mixture maintained at about ambient temperature followed by the addition of a reducing agent such as sodium cyanoborohydride and an alcohol such as methanol to provide 9.

solvent such as dichloromethane and treated with di-tert-butyldicarbonate or other suitable protecting group to obtain amine-protected compound 12. The N1-benzyl group can be removed to provide 13 via the transfer hydrogenation methodology described above in Scheme 3. N1 on the pyrimidinedione ring can then be alkylated by dissolving 13 in a polar, aprotic solvent such as DMF, then adding tetrabutylammonium bromide and an inorganic base such as NaOH to form a suspension which is maintained at elevated temperature (e.g., about 60 C) and then cooled to about ambient temperature. An alkylating agent such as a halide is then added, the resulting reaction mixture is maintained at elevated temperature (e.g., about 100 C) to form 14. Deprotection of the amine by treatment with an acid such as HCl provides 9.

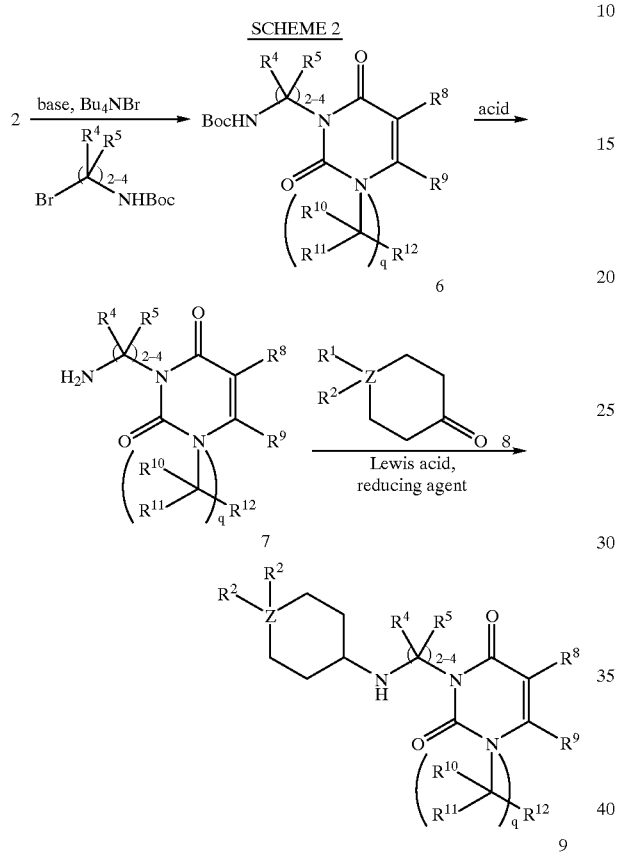

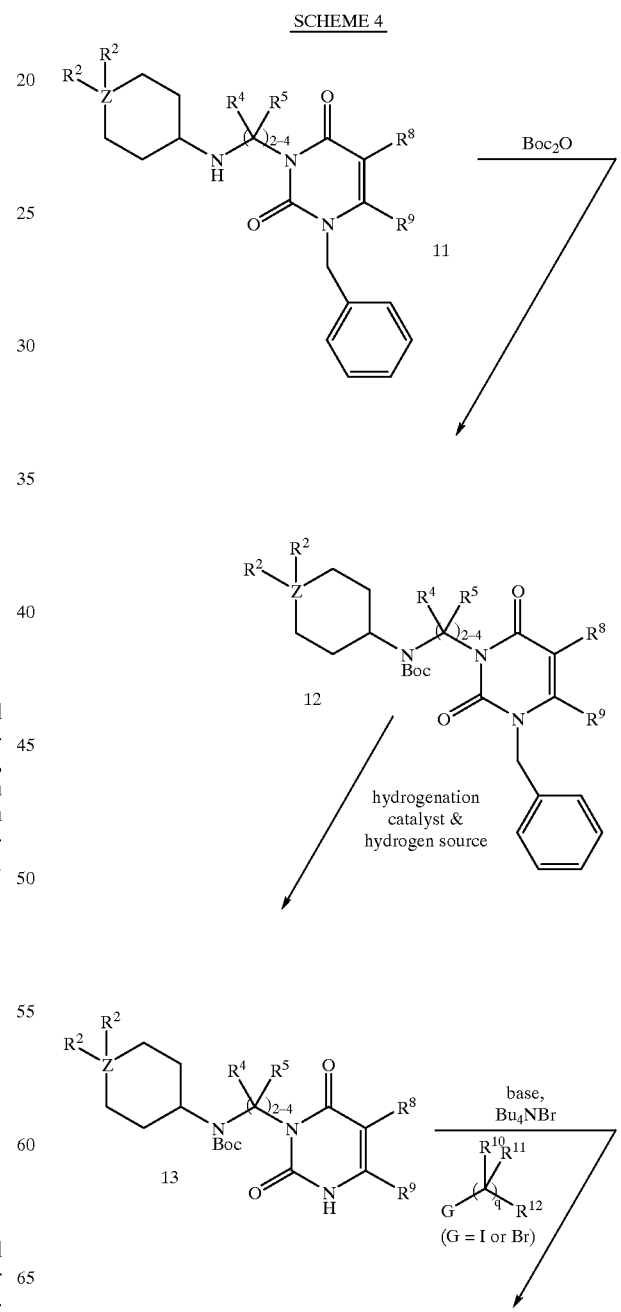

Scheme 3 describes the preparation of N1 unsubstituted pyrimidinedione compounds of the invention. An aminocyclohexyl or aminopiperidinyl compound of formula 9 (e.g., an N1-benzyl substituted compound) is dissolved in an alcohol (e.g., methanol) containing a hydrogen source such as ammonium formate, followed by addition of a hydrogenation catalyst (e.g., preferably 10% palladium on carbon). The resulting reaction mixture is refluxed to form 10.

Scheme 4 describes the preparation of N1-substituted derivatives of the invention from an aminocyclohexyl or aminopiperidinyl 1-benzyl-substituted pyrimidinedione precursor 11. Precursor 11 is dissolved in a polar, aprotic -continued

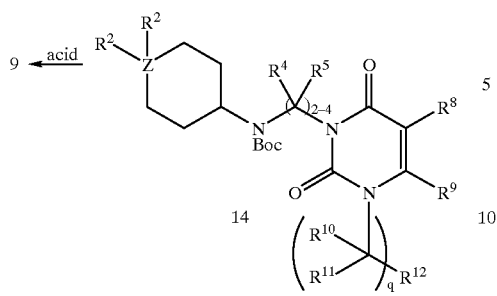

14

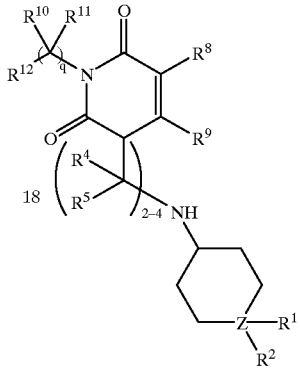

Scheme 5 describes the preparation of N3-substituted pyrimidinedione compounds of the invention. Pyrimidinedione 1 and an inorganic base such as potassium carbonate are suspended in a polar, aprotic solvent such as DMF. A bromide or iodide containing a protected amine (e.g., N-Boc-3-amino-1-5 bromopropane) is added to the suspension, and the resulting reaction mixture is maintained at about ambient temperature to obtain 15. The N3 in the pyrimidinedione ring can be alkylated via the alkylation procedure described in Scheme 4 to provide 16, which can be treated with an acid such as HCl to deprotect the amine to provide 17, which can be converted to 18 via the reductive alkylation procedure described in 10 Scheme 2.

Scheme 6 describes the preparation of 5-aryl substituted compounds of the invention. 5-Bromo-2,4(1H,3H)-pyrimidinedione 19 is suspended in a polar, aprotic solvent such as DMF. An inorganic base such as potassium carbonate is then added to the suspension, followed by a bromide or iodide (e.g., benzyl bromide). The resulting reaction mixture is maintained at about ambient temperature to form 20. N3 can be alkylated via the procedure described above in Scheme 4 to provide 21. An aryl group can be transferred to the 5-position of 23 via an arylzinc reagent through the mediation of Pd(0). Thus, an aryllithium is dissolved in an ether such as THF, cooled to below ambient temperature, and treated with a zinc salt (e.g., ZnCl$_2$). The reaction mixture is then warmed to about ambient temperature and treated with a source of Pd(0) (e.g., tetrakis(triphenylphosphine) palladium(0)) and compound 21 to obtain 22. Deprotection of 22 will form 23, which can be subjected to reductive alkylation as described in Scheme 2 to obtain 24.

SCHEME 5

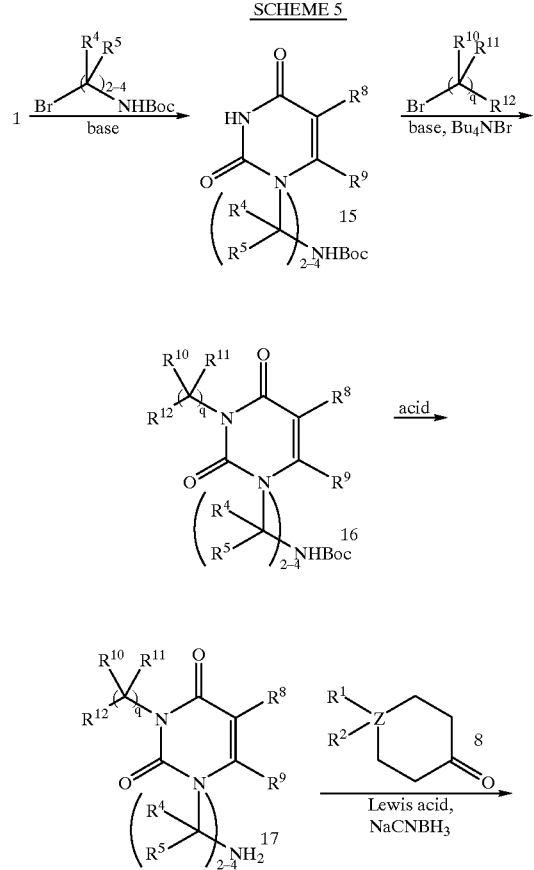

SCHEME 6

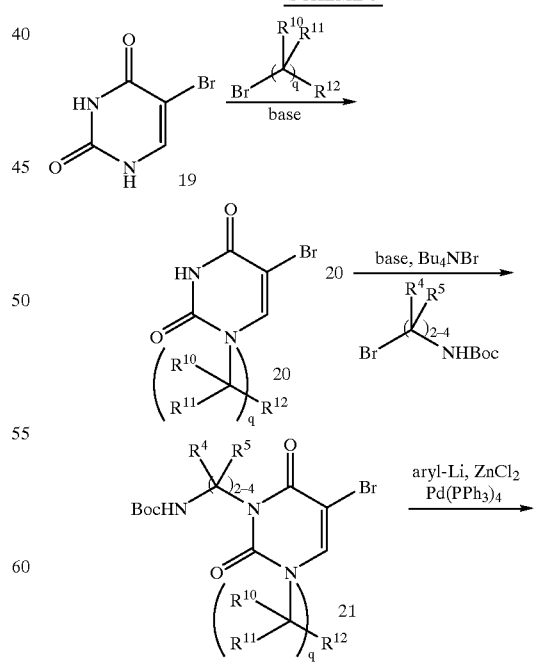

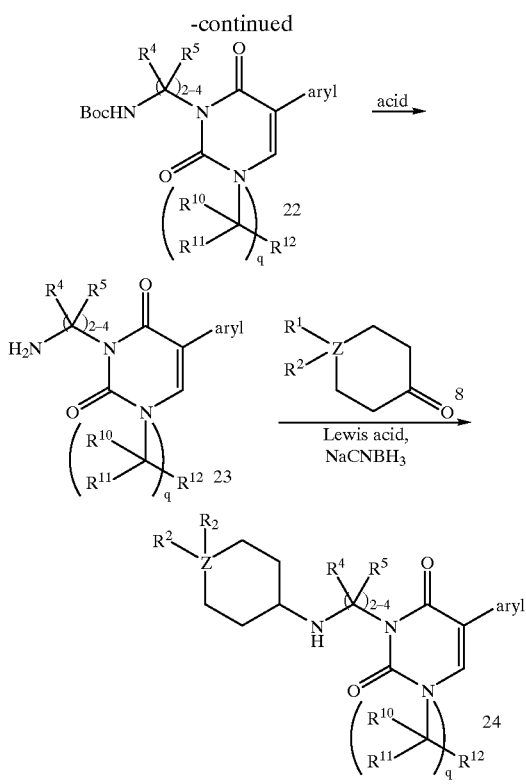

Precursors, intermediates, and compounds set forth in the foregoing schemes can be recovered and isolated via conventional filtration, extraction, and purification procedures.

The following Examples further describe and illustrate the invention and its practice and are not to be construed as limiting the scope or spirit of the invention.

EXAMPLE 1

1-Benzyl-3-{3-[4-(4-fluorophenyl)piperidin-1-yl]propyl}-5-methyl-1H-pyrimidine-2,4-dione Step A: 1-Benzyl-3-(3-bromopropyl)-5-methyl-1H-pyrimidine-2,4-dione To a solution of 1-benzyl-5-methyl-1H-pyrimidine-2,4-dione (1.0 g, 4.6 mmol) in N,N-dimethylformamide (15 mL) was added tetrabutylammonium bromide (60 mg, 0.2 mmol) and sodium hydroxide (200 mg, 5.1 mmol). The suspension was stirred vigorously, heated to 60° C. for 1.5 h and then cooled to ambient temperature. 1,3-Dibromopropane (0.5 mL, 5.1 mmol) was added, the reaction was heated to 50° C. for 16 h and then concentrated in vacuo. The residue was taken up in ethyl acetate:water (1:1 200 mL), the layers separated and the aqueous layer extracted with ethyl acetate (2×50 mL). The organic layers were combined and washed with 1 M sodium hydroxide (1×50 mL), water (1×50 mL), brine (1×100 mL), dried with magnesium sulfate, filtered and concentrated in vacuo. The resulting oil was purified by pressurized silica gel chromatography (25–30% ethyl acetate in hexane) to provide 1-benzyl-3-(3-bromopropyl)-5-methyl-1H-pyrimidine-2,4-dione.

Step B: 1-Benzyl-3-{3-[4-(4-fluorophenyl)piperidin-1-yl]propyl}-5-methyl-1H-pyrimidine-2,4-dione A suspension of 4-(4-fluorophenyl)piperidine hydrochloride (105 mg, 0.49 mmol) and 1-benzyl-3-(3-bromopropyl)-5-methyl-1H-pyrimidine-2,4-dione (164 mg, 0.49 mmol) in 20 mL acetonitrile was treated with sodium iodide (134 mg, 0.97 mmol) and potassium carbonate (100 mg, 0.73 mmol) and the reaction was heated at reflux for 16 h. The mixture was cooled to ambient temperature and poured into a separatory finnel containing water (100 mL) and dichloromethane (100 mL) and the layers separated. The aqueous layer was extracted with dichloromethane (2×100 mL) and the combined organics dried with magnesium sulfate, filtered and concentrated in vacuo to provide an oil. This crude material was purified by pressurized silica gel chromatography (5% methanol in ethyl acetate) to give 1-benzyl-3-{3-[4-(4-fluorophenyl)piperidin-1-yl]propyl}-5-methyl-1H-pyrimidine-2,4-dione (130 mg, 61%). The hydrochloride salt was prepared by conventional methods to provide a white solid.

Analysis: Calcd for C26 H30 N3 O2 F1.HCl.1.45 H2O,
C 62.69, H 6.86, N 8.44.
Found: C 62.31, H 6.52, N 8.07.

FAB MS: m/z=436 (M+H).

The compounds set forth in Examples 2 and 3 below were prepared by procedures substantially as described above for Example 1, Step B.

EXAMPLE 2

1-[3-(3-Benzyl-5-methyl-2,6-dioxo-3,6-dihydro-2H-pyrimidin-1-yl)propyl]-4-ortho-tolylpiperidine-4-carbonitrile

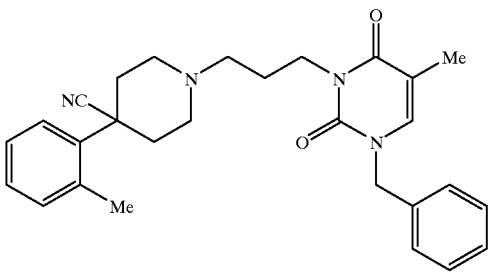

FAB MS: m/z=457 (M+H)

Analysis: Calcd for C28 H32 N4 O2.HCl.1.15 H2O,
C 65.45, H 6.93, N 10.91.
Found: C 65.43, H 6.68, N 10.98.

EXAMPLE 3

2-{1-[3-(3-Benzyl-5-methyl-2,6-dioxo-3,6-dihydro-2H-pyrimidin-1-yl)propyl]piperidin-4-yl}benzonitrile

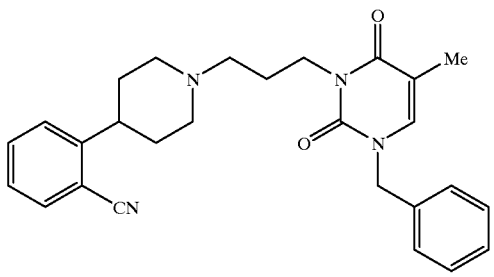

FAB MS: m/z=443 (M+H)

Analysis: Calcd for C27 H30 N4 O2.HCl.1.6H2O
C 63.85, H 6.79, N 11.03
Found: C 64.20, H 6.69, N 10.65

EXAMPLE 4 cis-4-[3-(3-Benzyl-5-methyl-2,6-dioxo-3,6-dihydro-2H-pyrimidin-1-yl)propylamino]-1-(2,4-difluorophenyl)cyclohexanecarbonitrile

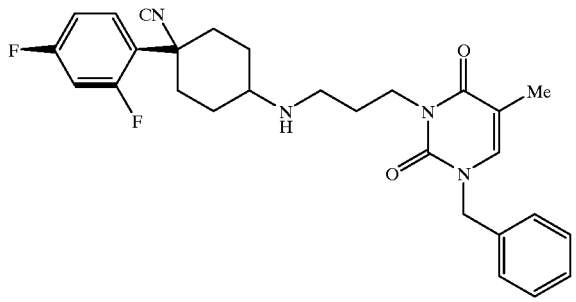

Step A: 3-(3-tert-Butoxycarbonylaminopropyl)-1-benzyl-5-methyl-1H-pyrimidine-2,4-dione To a solution of 1-benzyl-5-methyl-1H-pyrimidine-2,4-dione (1.0 g, 4.6 mmol) in N,N-dimethylformamide (15 mL) was added tetrabutylammonium bromide (60 mg, 0.2 mmol) and sodium hydroxide (200 mg, 5.1 mmol). The suspension was stirred vigorously, heated to 60° C. for 1.5 h and then cooled to ambient temperature. N-tert-butoxycarbonyl-3-bromopropylamine (1.2 g, 5.1 mmol) was added, the reaction was heated to 40° C. for 20 h and then concentrated in vacuo. The residue was taken up in ethyl acetate:water (1:1 200 mL), the layers separated and the aqueous layer extracted with ethyl acetate (4×50 mL). The organic layers were combined and washed with 0.5 M sodium hydroxide (1×50 mL), water (1×50 mL), brine (1×100 mL), dried with magnesium sulfate, filtered and concentrated in vacuo. The resulting oil was purified by pressurized silica gel chromatography (40% ethyl acetate in hexane) to provide 3-(3-tert-butoxycarbonylaminopropyl)-1-benzyl-5-methyl-1H-pyrimidine-2,4-dione.

Step B: 3-(3-Aminopropyl)-1-benzyl-5-methyl-1H-pyrimidine-2,4-dione

To a solution of 3-(3-tert-butoxycarbonylaminopropyl)-1-benzyl-5-methyl-1H-pyrimidine-2,4-dione (1.9 g, 4.5 mmol) in ethyl acetate (200 mL) at −78° C. was added HCl (g) for 5 min. The reaction was warmed to ambient temperature, the excess HCl removed by bubbling through nitrogen gas and then the reaction concentrated to provide the hydrochloride salt of 3-(3-aminopropyl)-1-benzyl-5-methyl-1H-pyrimidine-2,4-dione as a white solid.

Step C: cis-4-[3-(3-benzyl-5-methyl-2,6-dioxo-3,6-dihydro-2H-pyrimidin-1-yl)propylamino]-1-(2,4-difluorophenyl)cyclohexanecarbonitrile To a mixture of 3-(3-aminopropyl)-1-benzyl-5-methyl-1H-pyrimidine-2,4-dione hydrochloride (400 mg, 1.3 mmol) and 4-cyano-4-(2,4-difluorophenyl)cyclohexanone (270 mg, 1.2 mmol) in tetrahydrofuran (1 mL) under inert atmosphere was added N,N-diisopropylethylamine (230 mL, 1.3 mmol) and the reaction stirred 10 min. Titanium(IV) isopropoxide (510 mL, 1.7 mmol) was added, the reaction stirred 2 h when it was diluted with methanol (5 mL), treated with sodium cyanoborohydride (80 mg, 1.3 mmol) and stirred at ambient temperature 16 h. The reaction mixture was concentrated in vacuo, taken up in ethyl acetate (50 mL) and saturated sodium bicarbonate (50 mL), filtered through a pad of celite and the layers were separated. The organic layer was washed with water (1×50 mL), brine (1×50 mL), dried with magnesium sulfate, filtered and concentrated in vacuo. The crude material was purified by pressurized silica gel chromatography (2% methanol in ethyl acetate) to provide cis-4-[3-(3-benzyl-5-methyl-2,6-dioxo-3,6-dihydro-2H-pyrimidin-1-yl)propylamino]-1-(2,4-difluorophenyl)cyclohexanecarbonitrile and the trans isomer, Example 5.

FAB MS: m/z=493 (M+H)

Analysis: Calcd for C28 H30 N4 O2 F2.HCl.0.2H2O
C 63.14, H 5.94, N 10.52
Found: C 63.11, H 6.09, N 10.68.

EXAMPLE 5 trans-4-[3-(3-Benzyl-5-methyl-2,6-dioxo-3,6-dihydro-2H-pyrimidin-1-yl)propylamino]-1-(2,4-difluorophenyl)cyclohexanecarbonitrile

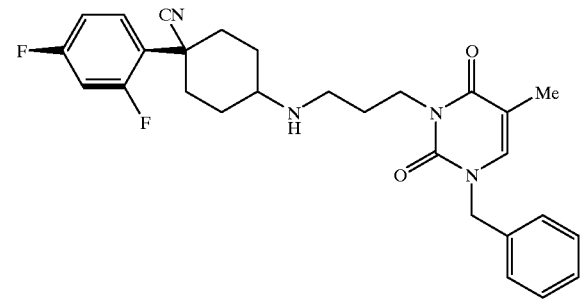

The title compound was prepared as described above in Example 4.

FAB MS: m/z=493 (M+H)

Analysis: Calcd for C28 H30 N4 O2 F2.HCl.0.5H2O
C 62.50, H 6.00, N 10.41
Found: C 62.47, H 6.02, N 10.97.

The compounds set forth in Example 6–18 were prepared by procedures substantially as described above in Example 4, Step C.

EXAMPLE 6 trans-4-[3-(3-Benzyl-5-methyl-2,6-dioxo-3,6-dihydro-2H-pyrimidin-1-yl)propylamino]-1-phenylcyclohexanecarbonitrile

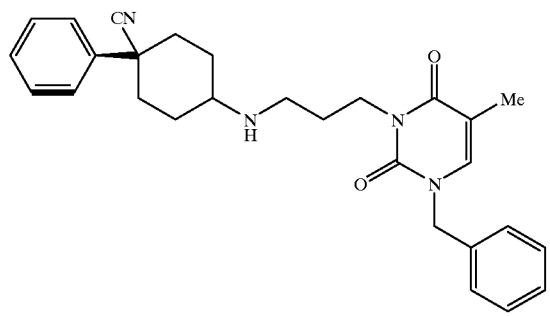

FAB MS: m/z=457 (M+H)

Analysis: Calcd for C28 H32 N4 O2.HCl.0.4H2O
C 67.22, H 6.81, N 11.20
Found: C 67.21, H 6.44, N 11.13.

EXAMPLE 7 cis-4-[3-(3-Benzyl-5-methyl-2,6-dioxo-3,6-dihydro-2H-pyrimidin-1-yl)propylamino]-1-phenylcyclohexanecarbonitrile

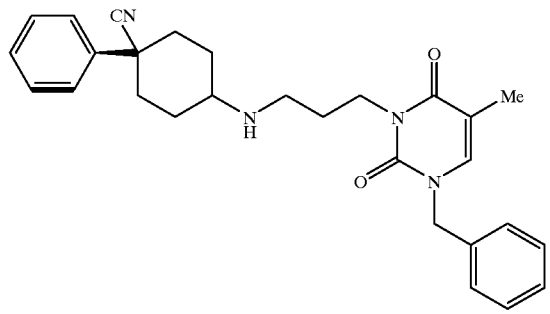

FAB MS: m/z=457 (M+H)

Analysis: Calcd for C28 H32 N4 O2.HCl.0.55H2O
C 66.86, H 6.83, N 11.14
Found: C 66.85, H 6.39, N 11.33.

EXAMPLE 8

1-Benzyl-3-{3-[1-(4-fluoro-2-methoxyphenyl)piperidin-4-ylamino]propyl}-5-methyl-1H-pyrimidine-2,4-dione

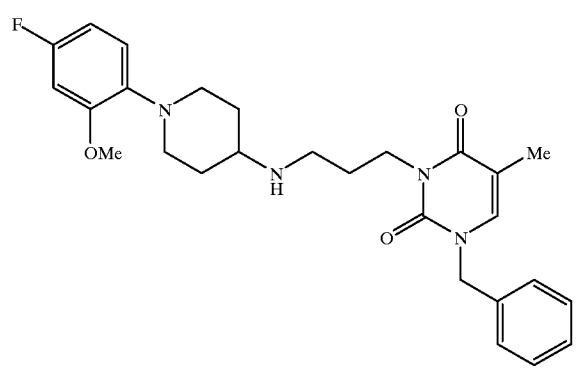

FAB MS: m/z=481 (M+H)

Analysis: Calcd for C27 H33 N4 O3 F1.HCl
C 62.72, H 6.63, N 10.84
Found: C 63.40, H 6.68, N 10.75.

EXAMPLE 9 cis-4-[3-(3-Benzyl-5-methyl-2,6-dioxo-3,6-dihydro-2H-pyrimidin-1-yl)propylamino]-1-(3,5-difluorophenyl)cyclohexanecarbonitrile

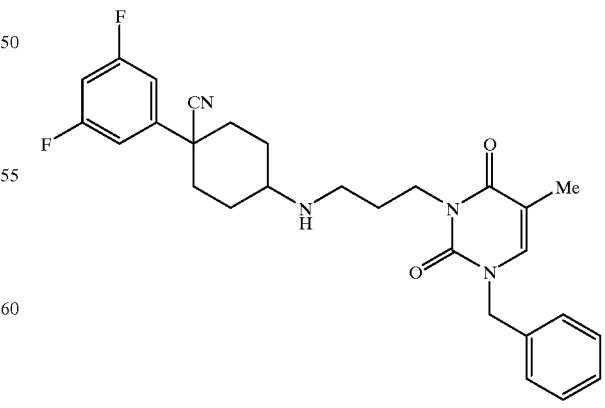

FAB MS: m/z=493 (M+H)

Analysis:. Calcd for C28 H30 N4 O2 F2.HCl.0.45H2O
C 62.61, H 5.99, N 10.43
Found: C 62.59, H 5.95, N 10.40.

EXAMPLE 10 cis-4-[3-(3-Benzyl-5-methyl-2,6-dioxo-3,6-dihydro-2H-pyrimidin-1-yl)propylamino]-1-(2-methoxyphenyl)cyclohexanecarbonitrile

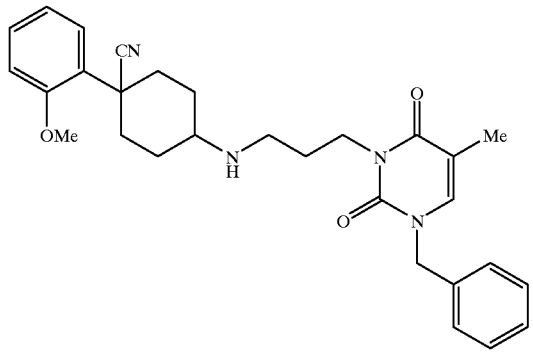

FAB MS: m/z=487 (M+H)

Analysis: Calcd for C29 H34 N4 O3.HCl
C 66.59, H 6.74, N 10.71
Found: C 66.14, H 7.01, N 10.31.

EXAMPLE 11 cis-4-[3-(3-benzyl-5-methyl-2,6-dioxo-3,6-dihydro-2H-pyrimidin-1-yl)propylamino]-1-(2-trifluoromethylphenyl)cyclohexanecarbonitrile

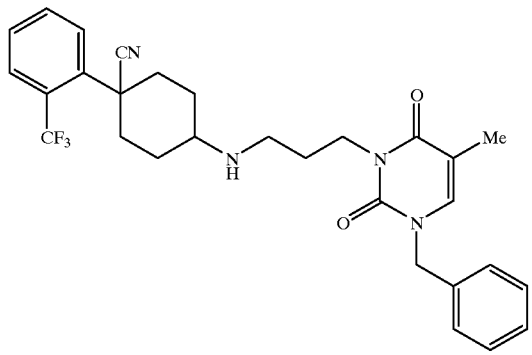

FAB MS: m/z=525 (M+H)

Analysis: Calcd for C29 H31 N4 O2 F3.HCl.0.65H2O
C 60.81, H 5.86, N 9.78
Found: C 60.52, H 5.56, N 9.14.

EXAMPLE 12 cis-4-[3-(3-Benzyl-5-methyl-2,6-dioxo-3,6-dihydro-2H-pyrimidin-1-yl)propylamino]-1-(4-fluoro-2-trifluoromethylphenyl)cyclohexanecarbonitrile

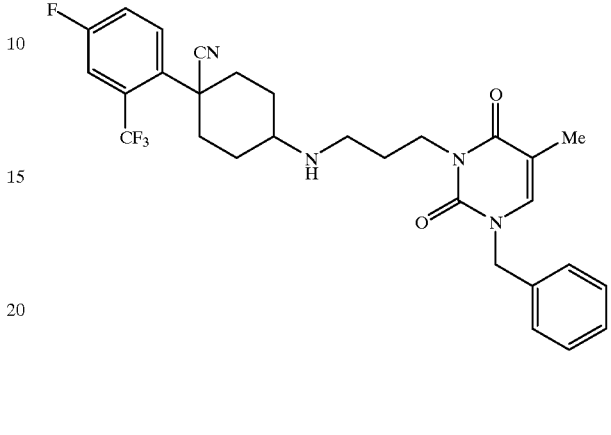

FAB MS: m/z=543 (M+H)

Analysis: Calcd for C29 H30 N4 O2 F4.HCl.0.9H2O
C 58.51, H 5.55, N 9.41
Found: C 58.47, H 5.53, N 9.10.

EXAMPLE 13 cis-4-[3-(3-Benzyl-5-methyl-2,6-dioxo-3,6-dihydro-2H-pyrimidin-1-yl)propylamino]-1-(2,4-dichlorophenyl)cyclohexanecarbonitrile

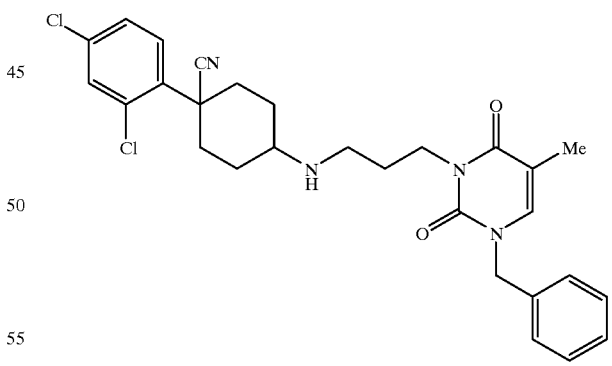

FAB MS: m/z=525 (M+H)

Analysis: Calcd for C28 H30 N4 O2 Cl2.HCl.0.95H2O
C 58.07, H 5.73, N 9.68
Found: C 57.88, H 5.24, N 9.60.

EXAMPLE 14 cis-2-{4-[3-(3-Benzyl-5-methyl-2,6-dioxo-3,6-dihydro-2H-pyrimidin-1-yl)propylamino]-1-cyanocyclohexyl}benzonitrile

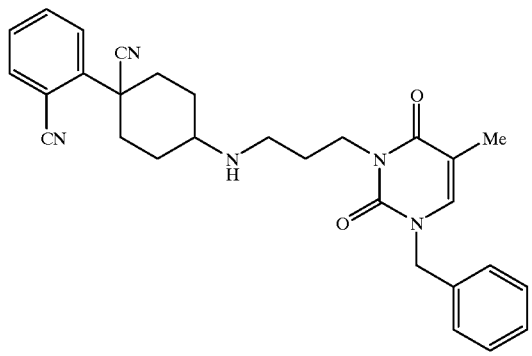

FAB MS: m/z=482 (M+H)

Analysis: Calcd for C29 H31 N5 O2.HCl.0.50H2O
C 66.08, H 6.31, N 13.29
Found: C 66.14, H 6.23, N 13.05.

EXAMPLE 15 cis-4-[3-(3-Benzyl-5-methyl-2,6-dioxo-3,6-dihydro-2H-pyrimidin-1-yl)propylamino]-1-(2-trifluoromethoxyphenyl)cyclohexanecarbonitrile

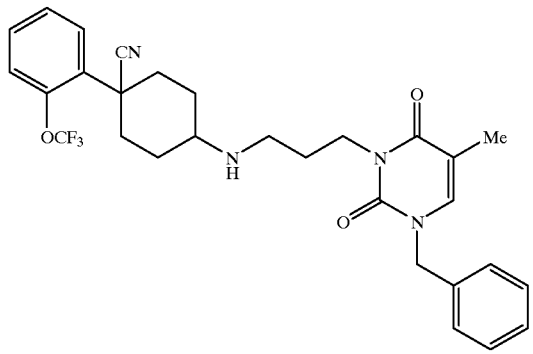

FAB MS: m/z=541 (M+H)

Analysis: Calcd for C29 H31 N4 O3 F3.HCl
C 60.36, H 5.59, N 9.71
Found: C 59.95, H 5.48, N 9.88.

EXAMPLE 16 cis-4-[3-(3-Benzyl-5-methyl-2,6-dioxo-3,6-dihydro-2H-pyrimidin-1-yl)propylamino]-1-pyridin-2-ylcyclohexanecarbonitrile

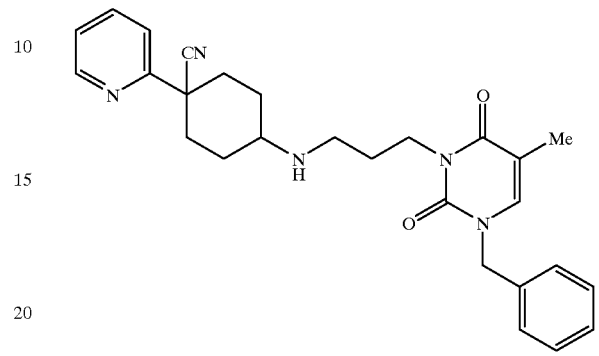

FAB MS: m/z=458 (M+H)

Analysis: Calcd for C27 H31 N5 O2.2HCl
C 61.13, H 6.27, N 13.20
Found: C 61.73, H 6.46, N 13.16.

EXAMPLE 17 trans-1-Benzyl-3-{3-[4-(2-methoxyphenyl)cyclohexylamino]propyl}-5-methyl-1H-pyrimidine-2,4-dione

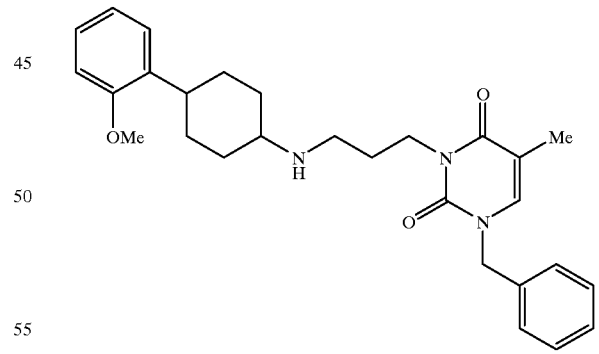

FAB MS: m/z=462 (M+H)

Analysis: Calcd for C28 H35 N3 O3.HCl.0.55H2O
C 66.20, H 7.36, N 8.27
Found: C 66.22, H 7.21, N 7.91.

EXAMPLE 18

2-{4-[3-(3-Benzyl-5-methyl-2,6-dioxo-3,6-dihydro-2H-pyrimidin-1-yl)propylamino]cyclohexyl}benzonitrile

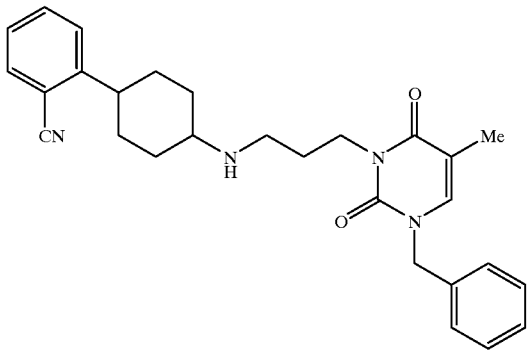

FAB MS: m/z=457 (M+H)

Analysis: Calcd for C28 H32 N4 O2.HCl.0.6H2O
C 66.74, H 6.84, N 11.12
Found: C 66.76, H 6.50, N 10.50.

EXAMPLE 19

3-{3-[1-(4-Fluoro-2-methoxyphenyl)piperidin-4-ylamino]propyl}-5-methyl-1H-pyrimidine-2,4-dione

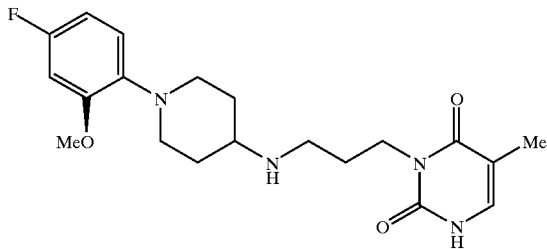

1-Benzyl-3-{3-[1-(4-fluoro-2-methoxyphenyl)piperidin-4-ylamino]propyl}-5-methyl-1H-pyrimidine-2,4-dione (Example 8) (100 mg, 0.2 mmol) was dissolved in a methanol solution of ammonium formate (0.1 M, 20 mL), treated with 10% palladium on carbon (100 mg) and the reaction heated to reflux for 24 h. The reaction mixture was filtered through a pad of celite, the filtrate concentrated and purified by pressurized silica gel chromatography (97.5:2:0.5 dichloromethane:methanol:ammonium hydroxide) to provide 3-{3-[1-(4-fluoro-2-methoxyphenyl)piperidin-4-ylamino]propyl}-5-methyl-1H-pyrimidine-2,4-dione. The hydrochloride salt was prepared according to conventional methods to provide a white solid.

FAB MS: m/z=391 (M+H)

Analysis: Calcd for C20 H27 N4 O3 F1.2HCl.2.5H2O
C 47.24, H 6.74, N 11.02
Found: C 47.26, H 6.47, N 10.28.

The compounds set forth in Examples 20 and 21 below were prepared by procedures substantially as described above in Example 19.

EXAMPLE 20 cis4-[3-(5-Methyl-2,6-dioxo-3,6-dihydro-2H-pyrimidin-1-yl)propylamino]-1-phenylcyclohexanecarbonitrile

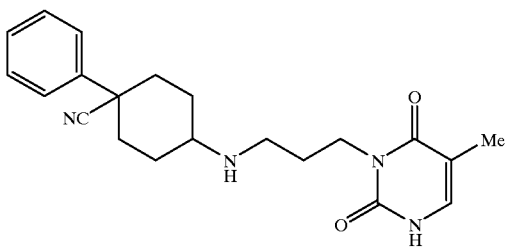

FAB MS: m/z=367 (M+H)

Analysis: Calcd for C21 H26 N4 O2.HCl.1.1H2O.0.75 dioxane
C 58.98, H 7.26, N 11.46
Found: C 58.71, H 6.93, N 11.45.

EXAMPLE 21 trans-4-[3-(5-Methyl-2,6-dioxo-3,6-dihydro-2H-pyrimidin-1-yl)propylamino]-1-phenylcyclohexanecarbonitrile

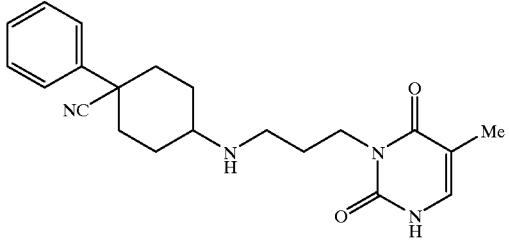

FAB MS: m/z=367 (M+H)

Analysis: Calcd for C21 H26 N4 O2.HCl.0.55H2O
C 61.09, H 6.86, N 13.57
Found: C 61.09, H 6.97, N 12.91.

EXAMPLE 22 cis-(3-{3-[4-Cyano-4-(2-cyanophenyl) cyclohexylamino]propyl}-5-methyl-2,4-dioxo-3,4-dihydro-2H-pyrimidin-1-yl) acetic acid methyl ester

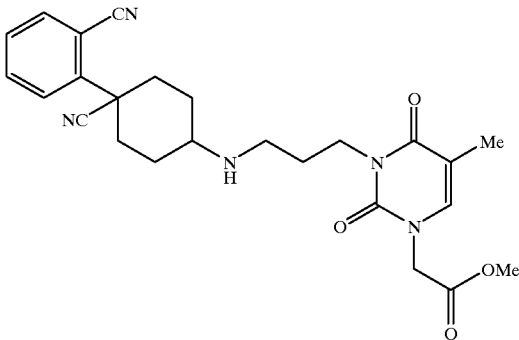

Step A: cis-2-{4-[3-(3-benzyl-5-methyl-2,6-dioxo-3,6-dihydro-2H-pyrimidin-1-yl)propyl-N-tert-butoxycarbonylamino]-1-cyanocyclohexyl}benzonitrile To a solution of cis-2-{4-[3-(3-benzyl-5-methyl-2,6-dioxo-3,6-dihydro-2H-pyrimidin-1-yl)propylamino]-1-cyanocyclohexyl}benzonitrile [prepared according to Example 14] (350 mg, 0.73 mml) in dichloromethane (25 mL) was added di-tert-butyldicarbonate (158 mg, 0.73 mmol) and the reaction stirred 20 h. The reaction mixture was concentrated and purified by pressurized silica gel chromatography to provide cis-2-{4-[3-(3-benzyl-5-methyl-2,6-dioxo-3,6-dihydro-2H-pyrimidin-1-yl)propyl-N-tert-butoxycarbonylamino]-1-cyanocyclohexyl}benzonitrile.

Step B: cis-2-{4-[3-(5-methyl-2,6-dioxo-3,6-dihydro-2H-pyrimidin-1-yl)propyl-N-tert-butoxycarbonylamino]-1-cyanocyclohexyl}benzonitrile cis-2-{4-[3-(3-benzyl-5-methyl-2,6-dioxo-3,6-dihydro-2H-pyrimidin-1-yl)propyl-N-tert-butoxycarbonylamino]-1-cyanocyclohexyl}benzonitrile (570 mg, 0.97 mmol) was dissolved in a methanol solution of ammonium formate (0.1 M, 80 mL), treated with 10% palladium on carbon (600 mg) and the reaction heated to reflux for 48 h. The reaction mixture was filtered over a pad of celite, the filtrate concentrated and purified by pressurized silica gel chromatography (ethyl acetate) to provide cis-2-{4-[3-(5-methyl-2,6-dioxo-3,6-dihydro-2H-pyrimidin-1-yl)propyl-N-tert-butoxycarbonylamino]-1-cyanocyclohexyl}benzonitrile.

Step C: cis-(3-{3-[4-cyano-4-(2-cyanophenyl)cyclohexyl-N-tert-butoxycarbonylamino]propyl}-5-methyl-2,4-dioxo-3,4-dihydro-2H-pyrimidin-1-yl) acetic acid methyl ester To a solution of cis-2-{4-[3-(5-methyl-2,6-dioxo-3,6-dihydro-2H-pyrimidin-1-yl)propyl-N-tert-butoxycarbonylamino]-1-cyanocyclohexyl} benzonitrile (80 mg, 0.17 mmol) in N,N-dimethylformamide (10 mL) was added tetrabutylammonium bromide (2 mg, 0.006 mmol) and sodium hydroxide (8 mg, 0.18 mmol). The reaction mixture was stirred vigorously, heated to 60° C. for 1.5 h and then cooled to ambient temperature. Methyl bromoacetate (20 mL, 0.18 mmol) was added, the reaction was heated to 50° C. for 24 h and then concentrated in vacuo. The residue was taken up in ethyl acetate:water (1:1 100 mL), the layers separated and the aqueous layer extracted with ethyl acetate (3×25 mL). The organic layers were combined and washed with 1 M sodium hydroxide (1×50 mL), water (1×50 mL), brine (1×100 mL), dried with magnesium sulfate, filtered and concentrated in vacuo. The resulting oil was purified by pressurized silica gel chromatography (2% methanol in ethyl acetate) to provide cis-(3-{3-[4-cyano-4-(2-cyanophenyl)cyclohexyl-N-tert-butoxycarbonylamino]propyl}-5-methyl-2,4-dioxo-3,4-dihydro-2H-pyrimidin-1-yl) acetic acid methyl ester.

Step D: cis-(3-{3-[4-cyano-4-(2-cyanophenyl) cyclohexylamino]propyl}-5-methyl-2,4-dioxo-3,4-dihydro-2H-pyrimidin-1-yl) acetic acid methyl ester To a solution of cis-(3-{3-[4-cyano-4-(2-cyanophenyl) cyclohexyl-N-tert-butoxycarbonylamino]propyl}-5-methyl-2,4-dioxo-3,4-dihydro-2H-pyrimidin-1-yl) acetic acid methyl ester (50 mg, 0.09 mmol) in ethyl acetate (25 mL) at −78° C. was added HCl (g) for 5 min. The reaction was warmed to ambient temperature, the excess HCl removed by bubbling through nitrogen gas and then the reaction concentrated to provide the hydrochloride salt of cis-(3-{3-[4-cyano4-(2-cyanophenyl)cyclohexylamino]propyl}-5-methyl-2,4-dioxo-3,4-dihydro-2H-pyrimidin-1-yl) acetic acid methyl ester as a white solid.

FAB MS: m/z=464 (M+H)

Analysis: Calcd for C25 H29 N5 O4.HCl.0.90H2O
C 58.16, H 6.21, N 13.57
Found: C 58.22, H6.30, N 13.46.

The compounds set forth in Examples 23 and 24 below were prepared by procedures substantially as described above in Example 22, Steps C and D.

EXAMPLE 23 cis-2-{1-Cyano-4-[3-(3,5-dimethyl-2,6-dioxo-3,6-dihydro-2H-pyrimidin-1-yl)propylamino] cyclohexyl}benzonitrile

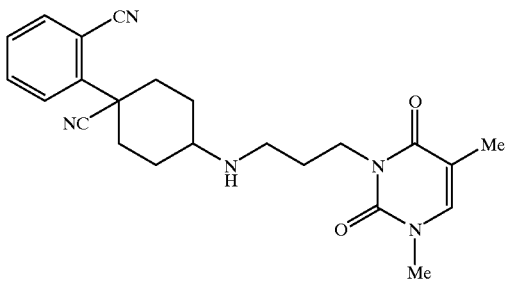

FAB MS: m/z=406 (M+H)

Analysis: Calcd for C23 H27 N5 O2.HCl.1.4H2O
C 59.13, H 6.65, N 14.99
Found: C 59.19, H 6.97, N 14.43.

EXAMPLE 24 cis-2-{1-Cyano-4-[3-(3-cyclopropylmethyl-5-methyl-2,6-dioxo-3,6-dihydro-2H-pyrimidin-1-yl)propylamino]cyclohexyl}benzonitrile

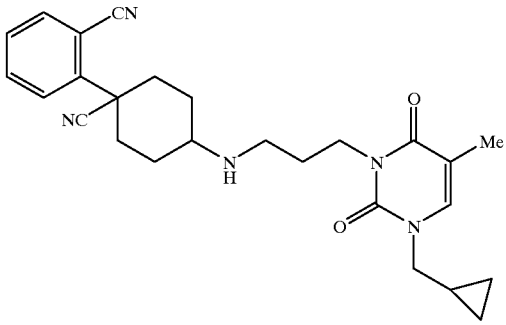

FAB MS: m/z=446 (M+H)

EXAMPLE 25 cis-2-{4-[3-(3-Benzyl-5-methyl-2,4-dioxo-3,4-dihydro-2H-pyrimidin-1-yl)propylamino]-1-cyanocyclohexyl}benzonitrile

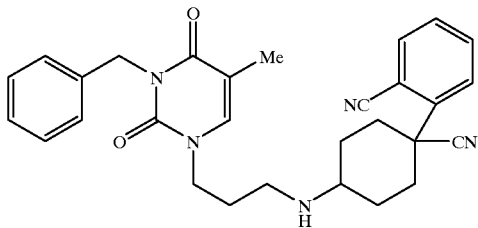

Step A: 1-(3-N-tert-butoxycarbonylaminopropyl)-5-methyl-1H-pyrimidine-2,4-dione

To a suspension of thymine (1.12 g, 8.2 mmol) and potassium carbonate (2.25 g, 16.3 mmol) in N,N-dimethylformamide (15 mL) was added N-tert-butoxycarbonyl-3-bromopropylamine (1.9 g, 8.2 mmol) and the reaction mixture stirred 20 h. The reaction was treated with water (50 mL) and then extracted into ethyl acetate (3×75 mL). The organic layers were combined, washed with water (2×50 mL), brine (1×50 mL), dried over magnesium sulfate, filtered and concentrated in vacuo. The resulting mixture of products was purified by pressurized silica gel chromatography (40% ethyl acetate in hexane) to provide 1-(3-N-tert-butoxycarbonylaminopropyl)-5-methyl-1H-pyrimidine-2,4-dione as a white solid.
FAB MS: m/z=284 (M+H)
Step B: 1-(3-N-tert-butoxycarbonylaminopropyl)-3-benzyl-5-methyl-1H-pyrimidine-2,4-dione To a solution of 1-(3-N-tert-butoxycarbonylaminopropyl)-5-methyl-1H-pyrimidine-2,4-dione (127 mg, 0.45 mmol) in N,N-dimethylformamide (5 mL) was added tetrabutylammonium bromide (6 mg, 0.02 mmol) and sodium hydroxide (20 mg, 0.50 mmol). The suspension was stirred vigorously, heated to 60° C. for 2 h and then cooled to ambient temperature. Benzyl bromide (160 mL, 1.3 mmol) was added, the reaction was heated to 50° C. for 24 h and then concentrated in vacuo. The residue was taken up in ethyl acetate:water (1:1 50 mL), the layers separated and the aqueous layer extracted with ethyl acetate (2×25 mL). The organic layers were combined and washed with 1 M sodium hydroxide (1×25 mL), water (1×25 mL), brine (1×25 mL), dried with magnesium sulfate, filtered and concentrated in vacuo. The resulting oil was purified by pressurized silica gel chromatography (40% ethyl acetate in hexane) to provide 1-(3-N-tert-butoxycarbonylaminopropyl)-3-benzyl-5-methyl-1H-pyrimidine-2,4-dione.

Step C: 1-(3-Aminopropyl)-3-benzyl-5-methyl-1H-pyrimidine-2,4-dione

To a solution of 1-(3-N-tert-butoxycarbonylaminopropyl)-3-benzyl-5-methyl-1H-pyrimidine-2,4-dione (151 mg, 0.4 mmol) in ethyl acetate (20 mL) at −78° C. was added HCl (g) for 5 min. The reaction was warmed to ambient temperature, the excess HCl removed by bubbling through nitrogen gas and then the reaction concentrated to provide the hydrochloride salt of 1-(3-aminopropyl)-3-benzyl-5-methyl-1H-pyrimidine-2,4-dione as a white solid.

Step D: cis-2-{4-[3-(3-benzyl-5-methyl-2,4-dioxo-3,4-dihydro-2H-pyrimidin-1-yl)propylamino]-1-cyanocyclohexyl}benzonitrile To a mixture of 1-(3-aminopropyl)-3-benzyl-5-methyl-1H-pyrimidine-2,4-dione hydrochloride (125 mg, 0.40 mmol) and 2-(1-cyano-4-oxocyclohexyl)benzonitrile (81 mg, 0.36 mmol) in tetrahydrofuran (1 mL) under inert atmosphere was added N,N-diisopropylethylamine (72 mL, 0.41 mmol) and the reaction stirred 10 min. Titanium(IV) isopropoxide (160 mL, 0.54 mmol) was added, the reaction stirred 2 h when it was diluted with methanol (5 mL), treated with sodium cyanoborohydride (25 mg, 0.39 mmol) and stirred at ambient temperature 20 h. The reaction was concentrated in vacuo, taken up in ethyl acetate (50 mL) and saturated sodium bicarbonate (50 mL) and filtered through a pad of celite. The organic phase was washed with water (1×50 mL), brine (1×50 mL), dried with magnesium sulfate, filtered and concentrated in vacuo. The crude material was purified by pressurized silica gel chromatography (5% methanol in ethyl acetate) to provide cis-2-{4-[3-(3-benzyl-5-methyl-2,4-dioxo-3,4-dihydro-2H-pyrimidin-1-yl)propylamino]-1-cyanocyclohexyl}benzonitrile and the trans - isomer, Example 26.
FAB MS: m/z=482 (M+H)

EXAMPLE 26 trans-2-{4-[3-(3-Benzyl-5-methyl-2,4-dioxo-3,4-dihydro-2H-pyrimidin-1-yl)propylamino]-1-cyanocyclohexyl}benzonitrile

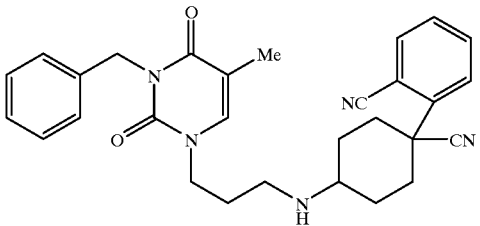

EXAMPLE 27 cis-2-{4-[3-(3-Benzyl-2,6-dioxo-5-phenyl-3,6-dihydro-2H-pyrimidin-1-yl)propylamino]-1-cyanocyclohexyl}benzonitrile

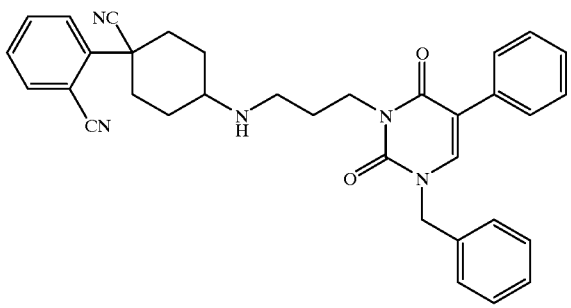

Step A: 1-Benzyl-5-bromo-1H-pyrimidine-2,4-dione

To a suspension of 5-bromouracil (5.0 g, 26 mmol) and potassium carbonate (7.2 g, 52 mmol) in N,N-dimethylformamide (25 mL) was added benzyl bromide (3.1 mL, 26 mmol) and the reaction mixture stirred 72 h. The reaction was treated with water (50 mL) and then extracted into ethyl acetate (3×75 mL). The aqueous layer was further extracted with dichloromethane (3×100 mL), the dichloromethane layers were combined, washed with water (2×50 mL), brine (1×50 mL), dried over magnesium sulfate, filtered and concentrated in vacuo. The resulting mixture of products was purified by pressurized silica gel chromatography (25% ethyl acetate in hexane) to provide 1-benzyl-5-bromo-1H-pyrimidine-2,4-dione.

Step B: 3-(3-tert-Butoxycarbonylaminopropyl)-1-benzyl-5-bromo-1H-pyrimidine-2,4-dione To a solution of 1-benzyl-5-bromo-1H-pyrimidine-2,4-dione (1.0 g, 3.6 mmol) in N,N-dimethylformamide (15 mL) was added tetrabutylammonium bromide (46 mg, 0.14 mmol) and sodium hydroxide (160 mg, 3.9 mmol). The suspension was stirred vigorously, heated to 60° C. for 1.5 h and then cooled to ambient temperature. N-tert-butoxycarbonyl-3-bromopropylamine (0.93 g, 3.9 mmol) was added, the reaction was heated to 50° C. for 20 h and then concentrated in vacuo. The residue was taken up in ethyl acetate:water (1:1 100 mL), the layers separated and the aqueous layer extracted with ethyl acetate (3×50 mL). The organic layers were combined and washed with 0.5 M sodium hydroxide (1×50 mL), water (1×50 mL), brine (1×100 mL), dried with magnesium sulfate, filtered and concentrated in vacuo. The resulting oil was purified by pressurized silica gel chromatography (40% ethyl acetate in hexane) to provide 3-(3-tert-butoxycarbonylaminopropyl)-1-benzyl-5-bromo-1H-pyrimidine-2,4-dione.

Step C: 3-(3-tert-Butoxycarbonylaminopropyl)-1-benzyl-5-phenyl-1H-pyrimidine-2,4-dione A solution of zinc chloride (0.5 M in tetrahydrofuran, 2.3 mL, 1.1 mL) and a solution of phenyllithium (1.8 M in tetrahydrofuran, 3.2 mL, 5.7 mmol) were stirred together at −78° C. under inert atmosphere for 10 min when the reaction was warmed to ambient temperature. Tetrakis(triphenylphosphine)palladium(0) (66 mg, 0.057 mmol) and 3-(3-tert-butoxycarbonylaminopropyl)-1-benzyl-5-bromo-1H-pyrimidine-2,4-dione (500 mg, 1.1 mmol) were added and the reaction stirred at ambient temperature 20 h. The reaction mixture was treated with saturated sodium bicarbonate (50 mL) and extracted into ethyl acetate (3×50 mL). The organic layers were combined, dried over magnesium sulfate, filtered and concentrated in vacuo. The resulting mixture was purified by pressurized silica gel chromatography (25–35% ethyl acetate in hexane) to provide 3-(3-tert-butoxycarbonylaminopropyl)-1-benzyl-5-phenyl-1H-pyrimidine-2,4-dione.

Step D: 3-(3-Aminopropyl)-1-benzyl-5-phenyl-1H-pyrimidine-2,4-dione

To a solution of 3-(3-tert-butoxycarbonylaminopropyl)-1-benzyl-5-phenyl-1H-pyrimidine-2,4-dione (160 mg, 0.37 mmol) in ethyl acetate (20 mL) at −78° C. was added HCl (g) for 5 min. The reaction was warmed to ambient temperature, the excess HCl removed by bubbling through nitrogen gas and then the reaction concentrated to provide the hydrochloride salt of 3-(3-aminopropyl)-1-benzyl-5-phenyl-1H-pyrimidine-2,4-dione as a white solid.

Step E: cis-2-{4-[3-(3-benzyl-2,6-dioxo-5-phenyl-3,6-dihydro-2H-pyrimidin-1-yl)propylamino]-1-cyanocyclohexyl}benzonitrile To a mixture of 3-(3-aminopropyl)-1-benzyl-5-phenyl-1H-pyrimidine-2,4-dione hydrochloride (130 mg, 0.36 mmol) and 2-(1-cyano-4-oxocyclohexyl)benzonitrile (81 mg, 0.36 mmol) in tetrahydrofuran (1 mL) under inert atmosphere was added N,N-diisopropylethylamine (72 mL, 0.41 mmol) and the reaction stirred 10 min. Titanium(IV) isopropoxide (160 mL, 0.54 mmol) was added, the reaction stirred 2 h when it was diluted with methanol (5 mL), treated with sodium cyanoborohydride (25 mg, 0.39 mmol) and stirred at ambient temperature 20 h. The reaction was concentrated in vacuo, taken up in ethyl acetate (50 mL) and saturated sodium bicarbonate (50 mL), filtered through a pad of celite, and the layers were separated. The organic layer was washed with water (1×50 mL), brine (1×50 mL), dried with magnesium sulfate, filtered and concentrated in vacuo. The crude material was purified by pressurized silica gel chromatography (5% methanol in ethyl acetate) to provide cis-2-{4-[3-(3-benzyl-2,6-dioxo-5-phenyl-3,6-dihydro-2H-pyrimidin-1-yl)propylamino]-1-cyanocyclohexyl}benzonitrile and the trans -isomer, Example 28.

FAB MS: m/z=544 (M+H)

EXAMPLE 28 trans-2-{4-[3-(3-Benzyl-2,6-dioxo-5-phenyl-3,6-dihydro-2H-pyrimidin-1-yl)propylamino]-1-cyanocyclohexyl}benzonitrile

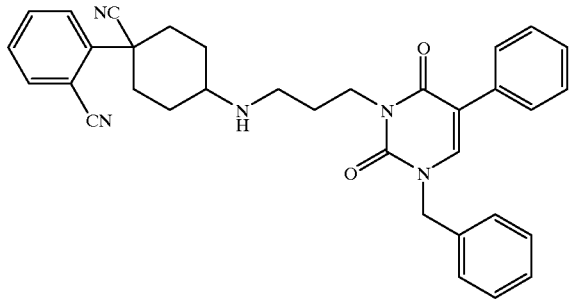

The title compound was prepared as described in Example 27.

FAB MS: m/z=544 (M+H)

EXAMPLE 29

As a specific embodiment of an oral composition, 100 mg of the compound of Example 14 is formulated with sufficient finely divided lactose to provide a total amount of 580 to 590 mg to fill a size O hard gel capsule.

EXAMPLE 30

Screening Assay: Alpha 1a Adrenergic Receptor Binding

Membranes prepared from the stably transfected human alpha 1a cell line (ATCC CRL 11140) were used to identify compounds that bind to the human alpha 1a adrenergic receptor. These competition binding reactions (total volume=200 μl) contained 50 mM Tris-HCl pH. 7.4, 5 mM EDTA, 150 mM NaCl, 100 pM [$^{125}$I]-HEAT, membranes prepared from the alpha 1a cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

EXAMPLE 31

Selective Binding Assays

Membranes prepared from stably transfected human alpha 1d and alpha 1b cell lines (ATCC CRL 11138 and CRL 11139, respectively) were used to identify compounds that selectively bind to the human alpha 1a adrenergic receptor. These competition binding reactions (total volume=200 μl) contained 50 mM Tris-HCl pH. 7.4, 5 mM EDTA, 150 mM NaCl, 100 pM [$^{125}$I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

All of the compounds of the present invention prepared in Examples 1–28 were found to have alpha 1a Ki values of less than 30 nM, as determined via the screening assay described in Example 30, except for the compounds set forth in Example 6 (500 nM), Example 9 (115 mM), Example 21 (755 nM), and Example 26 (790 nM). All of the compounds were further found to be more selective in binding to alpha 1a receptors versus binding to alpha 1b and alpha 1d receptors, as determined via the selective binding assay described in the preceding paragraph. All of the compounds were found to be greater than 10-fold more selective in binding to alpha 1a receptors versus binding to the alpha 1b and alpha 1d receptors, except for the compounds of Examples 1, 2, 4–6, 9, 17, 20, 21, and 26.

EXAMPLE 32

Examplary Counterscreens

1. Assay Title: Dopamine D2, D3, D4 In Vitro Screen
Objective of the Assay:
The objective of this assay is to eliminate agents which specifically affect binding of [3H] spiperone to cells expressing human dopamine receptors D2, D3 or D4.
Method:
Modified from VanTol et al., *Nature* (1991), 350: 610–613.

Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15' at 24,450 rpm) are resuspended in 5 mM Tris-HCl pH 7.4 containing EDTA, MgCl[2], KCl, NaCl, CaCl[2] and ascorbate to give a 1 Mg/mL suspension. The assay is initiated by adding 50–75 μg membranes in a total volume of 500 μl containing 0.2 nM [3H]-spiperone. Non-specific binding is defined using 10 μM apomorphine. The assay is terminated after a 2 hour incubation at room temperature by rapid filtration over GF/B filters presoaked in 0.3% PEI, using 50 mM Tris-HCl pH 7.4.

2. Assay Title: Serotonin 5HT1a
Obiective of the Assay
The objective of this assay is to eliminate agents which specifically affect binding to cloned human 5HT1a receptor
Method:
Modified from Schelegel and Peroutka, *Biochemical Pharmacology* (1986), 35: 1943–1949.

Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 100×g for 30', and then the supernatant is centrifuged again at 38,00×g for 30'. The binding assay contains 0.25 nM [3H]8-OH-DPAT (8-hydroxy-2-dipropylamino-1,2,3,4-tetrahydronaphthalene) in 50 mM Tris-HCl, 4 mM CaCl2 and 1 mg/ml ascorbate. Non-specific binding is defined using 10 μM propranolol. The assay is terminated after a 1 hour incubation at room temperature by rapid filtration over GF/Cfilters.

EXAMPLE 33

Examplary Functional Assays

In order to confirm the specificity of compounds for the human alpha 1a adrenergic receptor and to define the biological activity of the compounds, the following functional tests may be performed:
1. In Vitro Rat, Dog and Human Prostate and Dog Urethra Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% $CO_2$/95% $O_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 μM (for rat), 10 μM (for dog) and 20 μM (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.

$EC_{50}$ values are calculated for each group using GraphPad Inplot software. $pA_2$ ($-\log K_b$) values were obtained from Schild plot when three or more concentrations were tested. When less than three concentrations of antagonist are tested, $K_b$ values are calculated according to the following formula $K_b = [B]$, $$\frac{1}{x-1}$$

where x is the ratio of $EC_{50}$ of agonist in the presence and absence of antagonist and [B] is the antagonist concentration.

2. Measurement of Intra-Urethral Pressure in Anesthetized Dogs

PURPOSE:

Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha 1 receptor antagonists which also have pronounced vascular effects. Because we have identified the alpha 1a receptor subtype as the predominant subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha 1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS:

Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha 1adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four paramenter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha 1antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonists that prevent the increase in intra-urethral pressure to phenylephrine without any activity at the vasculature.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A compound of formula:

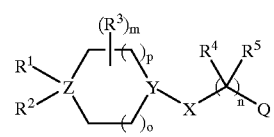

wherein Q is

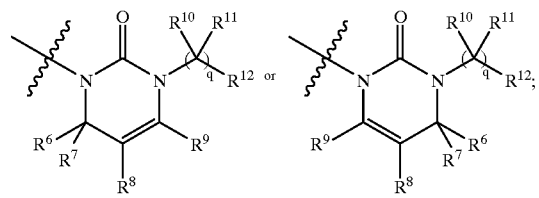

Z is C or N, provided that when Z is N, $R^2$ is absent;

X is $CR^aR^b$ or $NR^a$;

Y is CH or N; provided that when Y is N, Z is C and X is $CR^aR^b$; and provided that when Y is CH, X is $NR^a$;

$R^1$ is phenyl, mono- or poly-substituted phenyl, pyridyl, mono- or poly-substituted pyridyl, thienyl, or mono- or poly-substituted thienyl; wherein each of the substituents on the substituted phenyl is independently selected from halo, nitro, cyano, hydroxy, amino, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, $C(=O)N(R^c)_2$ and $SO_2N(R^c)_2$; each of the substituents on the substituted pyridyl is independently selected from halo, cyano, hydroxy, amino, $C_1$–$C_6$ alkyl, $C_1$–$C_6$ alkoxy, fluorinated $C_1$–$C_6$ alkyl, fluorinated $C_1$–$C_6$ alkoxy, $CO_2R^c$, $C(=O)N(R^c)_2$ and $SO_2N(R^c)_2$; and each of the substituents on the substituted thienyl is independently selected from halo, $C_1$–$C_6$ alkyl, and fluorinated $C_1$–$C_6$ alkyl;

$R^2$ is hydrogen, cyano, hydroxy, $CO_2R^c$, $C(=O)N(R^c)_2$, $NR^cC(=O)R^c$, $NR^cSO_2R^c$, phenyl, mono- or poly-substituted phenyl, pyridyl, mono- or poly-substituted pyridyl, thienyl, or mono- or poly-substituted thienyl; wherein each of the substituents on the substituted phenyl is independently selected from halo, nitro, cyano, hydroxy, amino, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, $C(=O)N(R^c)_2$ and $SO_2N(R^c)_2$; each of the substituents on the substituted pyridyl is independently selected from halo, cyano, hydroxy, amino, $C_1$–$C_6$ alkyl, $C_1$–$C_6$ alkoxy, fluorinated $C_1$–$C_6$ alkyl, fluorinated $C_1$–$C_6$ alkoxy, $CO_2R^c$, $C(=O)N(R^c)_2$ and $SO_2N(R^c)_2$; and each of the substituents on the substituted thienyl is independently selected from halo, $C_1$–$C_6$ alkyl, and fluorinated $C_1$–$C_6$ alkyl;

each $R^3$ is a substituent at a ring atom other than Z or Y and is independently $C_1$–$C_4$ alkyl;

$R^4$, $R^5$, $R^{10}$ and $R^{11}$ are each independently selected from hydrogen, $C_1$–$C_6$ alkyl, and $C_3$–$C_8$ cycloalkyl;

$R^6$ and $R^7$ are taken together to form oxo;

$R^8$ and $R^9$ are each independently selected from hydrogen, halo, cyano, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, $C(=O)R^c$, $C(=O)N(R^c)_2$, phenyl, mono- or poly-substituted phenyl, pyridyl, mono- or poly-substituted pyridyl, thienyl, and mono- or poly-substituted thienyl; wherein each of the substituents on the substituted phenyl is independently selected from halo, nitro, cyano, hydroxy, amino, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, $C(=O)N(R^c)_2$ and $SO_2N(R^c)_2$; each of the substituents on the substituted pyridyl is independently selected from halo, cyano, hydroxy, amino, $C_1$–$C_6$ alkyl, $C_1$–$C_6$ alkoxy, fluorinated $C_1$–$C_6$ alkyl, fluorinated $C_1$–$C_6$ alkoxy, $CO_2R^c$, $C(=O)N(R^c)_2$ and $SO_2N(R^c)_2$; and each of the substituents on the substituted thienyl is independently selected from halo, $C_1$–$C_6$ alkyl, and fluorinated $C_1$–$C_6$ alkyl;

$R^{12}$ is hydrogen, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, phenyl, mono- or poly-substituted phenyl, pyridyl, mono- or poly-substituted pyridyl, thienyl, mono- or poly-substituted thienyl,

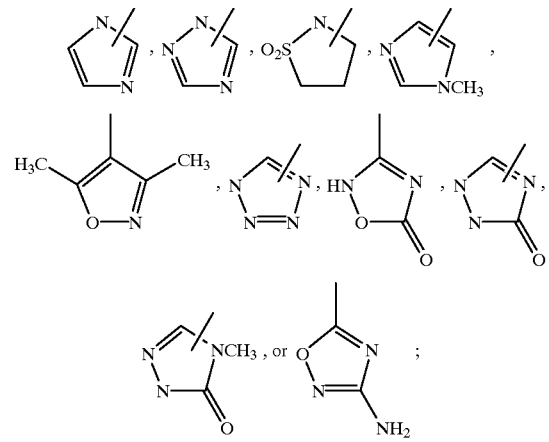

wherein each of the substituents on the substituted phenyl is independently selected from halo, nitro, cyano, hydroxy, amino, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, $C(=O)N(R^c)_2$ and $SO_2N(R^c)_2$; each of the substituents on the substituted pyridyl is independently selected from halo, cyano, hydroxy, amino, $C_1$–$C_6$ alkyl, $C_1$–$C_6$ alkoxy, fluorinated $C_1$–$C_6$ alkyl, fluorinated $C_1$–$C_6$ alkoxy, $CO_2R^c$, $C(=O)N(R^c)_2$ and $SO_2N(R^c)_2$; and each of the substituents on the substituted thienyl is independently selected from halo, $C_1$–$C_6$ alkyl, fluorinated $C_1$–$C_6$ alkyl;

$R^a$ and $R^b$ are each independently selected from hydrogen, $C_1$–$C_6$ alkyl, and $C_3$–$C_8$ cycloalkyl;

$R^c$ is hydrogen or $C_1$–$C_6$ alkyl;

m is an integer of from 0 to 4;

n is an integer of from 2 to 4, when X is $NR^a$;

n is an integer of from 1 to 3, when X is $CR^aR^b$;

o and p are each integers of from 0 to 2, wherein the sum of o+p is less than or equal to 3; and q is an integer of from 0 to 2;

or a pharmaceutically acceptable salt thereof.

2. The compound according to claim 1, wherein $R^1$ is phenyl; mono-, di- or tri-substituted phenyl; pyridyl; mono- or di-substituted pyridyl; thienyl; or mono-substituted thienyl;

$R^2$ is hydrogen, cyano, hydroxy, $CO_2R^c$, $C(=O)N(R^c)_2$, $NR^cC(=O)R^c$, $NR^cSO_2R^c$, phenyl, mono- or di- or tri-substituted phenyl, pyridyl, mono- or di-substituted pyridyl, thienyl, or mono-substituted thienyl;

$R^4$ and $R^5$ are either both hydrogen, or one of $R^4$ and $R^5$ is hydrogen and the other is hydrogen, $C_1$–$C_6$ alkyl, or $C_3$–$C_8$ cycloalkyl;

$R^8$ and $R^9$ are each independently selected from hydrogen, halo, cyano, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, $C(=O)R^c$, $C(=O)N(R^c)_2$, phenyl, mono- or di-substituted phenyl, pyridyl, mono- or di-substituted pyridyl, thienyl and mono-substituted thienyl; and $R^{10}$ and $R^{11}$ are either both hydrogen, or one of $R^{10}$ and $R^{11}$ is hydrogen and the other is $C_1$–$C_6$ alkyl or $C_3$–$C_8$ cycloalkyl; and $R^{12}$ is hydrogen, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $CO_2R^c$, phenyl, mono- or di-substituted phenyl, pyridyl, mono- or di-substituted pyridyl, thienyl, or mono-substituted thienyl,

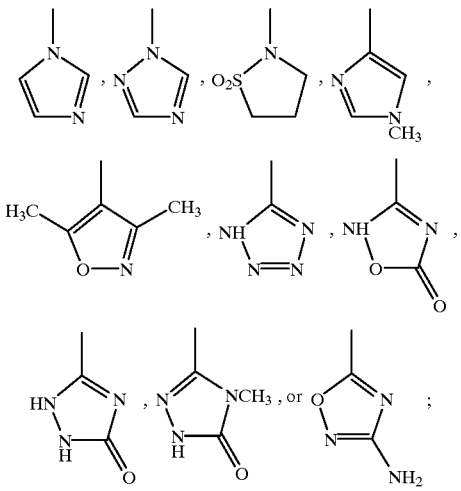

or a pharmaceutically acceptable salt thereof.

3. The compound according to claim 2, wherein in $R^1$ each substituent on the substituted phenyl is independently selected from halo, nitro, cyano, hydroxy, amino, $C_1$–$C_4$ alkyl, $C_3$–$C_6$ cycloalkyl, $C_1$–$C_4$ alkoxy, fluorinated $C_1$–$C_4$ alkyl, fluorinated $C_3$–$C_6$ cycloalkyl, fluorinated $C_1$–$C_4$ alkoxy, $CO_2R^c$, $C(=O)N(R^c)_2$ and $SO_2N(R^c)_2$; each substituent on the substituted pyridyl is independently selected from halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$; and each substituent on the substituted thienyl is independently selected from halo and $C_1$–$C_4$ alkyl;

in $R^2$ each substituent on the substituted phenyl is independently selected from halo, nitro, cyano, hydroxy, amino, $C_1$–$C_4$ alkyl, $C_3$–$C_6$ cycloalkyl, $C_1$–$C_4$ alkoxy, fluorinated $C_1$–$C_4$ alkyl, fluorinated $C_3$–$C_6$ cycloalkyl, fluorinated $C_1$–$C_4$ alkoxy, $CO_2R^c$, $C(=O)N(R^c)_2$ and $SO_2N(R^c)_2$; each substituent on the substituted pyridyl is independently selected from halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$; and each substituent on the substituted thienyl is independently selected from halo and $C_1$–$C_4$ alkyl;

in $R^8$ and $R^9$ each substituent on the substituted phenyl is independently selected from halo, nitro, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$; each substituent on the substituted pyridyl is independently selected from halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$; and each substituent on the substituted thienyl is independently selected from halo and $C_1$–$C_4$ alkyl; and in $R^{12}$ each substituent on the substituted phenyl is independently selected from halo, nitro, cyano, hydroxy, amino, $C_1$–$C_4$ alkyl, $C_3$–$C_6$ cycloalkyl, $C_1$–$C_4$ alkoxy, fluorinated $C_1$–$C_4$ alkyl, fluorinated $C_3$–$C_6$ cycloalkyl, fluorinated $C_1$–$C_4$ alkoxy, $CO_2R^c$, $C(=O)N(R^c)_2$ and $SO_2N(R^c)_2$; each substituent on the substituted pyridyl is independently selected from halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$; and each substituent on the substituted thienyl is independently selected from halo and $C_1$–$C_4$ alkyl;

or a pharmaceutically acceptable salt thereof.

4. The compound according to claim 3, wherein each of $R^4$, $R^5$, $R^{10}$ and $R^{11}$ is hydrogen; and m is 0;

or a pharmaceutically acceptable salt thereof.

5. The compound according to claim 1, wherein the compound is of formula:

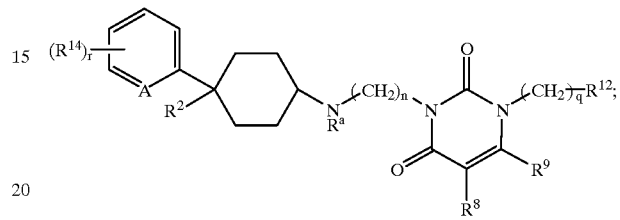

wherein A is C—$R^{14}$ or N;

$R^2$ is hydrogen, cyano, hydroxy, $CO_2R^c$, $C(=O)N(R^c)_2$, $NR^cC(=O)R^c$ or $NR^cSO_2R^c$;

$R^8$ and $R^9$ are each independently selected from hydrogen, halo, cyano, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)R^c$, $C(=O)N(R^c)_2$, phenyl, and mono- or di-substituted phenyl; wherein each substituent on the substituted phenyl is independently selected from fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ and $SO_2NH_2$;

$R^{12}$ is hydrogen, $C_1$–$C_4$ alkyl, $C_3$–$C_6$ cycloalkyl, $C_1$–$C_4$ alkoxy, fluorinated $C_1$–$C_4$ alkyl, fluorinated $C_1$–$C_4$ alkoxy, $CO_2R^c$, phenyl, or mono- or di-substituted phenyl; wherein each substituent on the substituted phenyl is independently selected from halo, nitro, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$;

each $R^{14}$ is independently hydrogen, halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ or $SO_2N(R^c)_2$;

$R^a$ is hydrogen or $C_1$–$C_6$ alkyl;

$R^c$ is hydrogen or $C_1$–$C_4$ alkyl; and r is an integer of from 0 to 2;

or a pharmaceutically acceptable salt thereof.

6. The compound according to claim 5, wherein the compound is selected from the group consisting of cis-4-[3-(5-methyl-2,6-dioxo-3,6-dihydro-2H-pyrimidin-1-yl)propylamino]-1-phenylcyclohexanecarbonitrile;

trans-4-[3-(5-methyl-2,6-dioxo-3,6-dihydro-2H-pyrimidin-1-yl)propylamino]-1-phenylcyclohexanecarbonitrile;

cis-(3-{3-[4-cyano-4-(2-cyanophenyl)cyclohexylamino]propyl}-5-methyl-2,4-dioxo-3,4-dihydro-2H-pyrimidin-1-yl) acetic acid methyl ester;

cis-2-{1-cyano-4-[3-(3,5-dimethyl-2,6-dioxo-3,6-dihydro-2H-pyrimidin-1-yl)propylamino]cyclohexyl}benzonitrile;

cis-2-{1-cyano-4-[3-(3-cyclopropylmethyl-5-methyl-2,6-dioxo-3,6-dihydro-2H-pyrimidin-1-yl)propylamino]cyclohexyl}benzonitrile; and
pharmaceutically acceptable salts thereof.

7. The compound according to claim 5, wherein $R^{12}$ is of formula:

wherein each $R^{16}$ is independently hydrogen, fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ or $SO_2NH_2$;

q is 1; and s is an integer of from 0 to 2;

or a pharmaceutically acceptable salt thereof.

8. The compound according to claim 1, wherein the compound is selected from the group consisting of trans-4-[3-(3-benzyl-5-methyl-2,6-dioxo-3,6-dihydro-2H-pyrimidin-1-yl)propylamino]-1-(2,4-difluorophenyl)cyclohexanecarbonitrile;

trans-4-[3-(3-benzyl-5-methyl-2,6-dioxo-3,6-dihydro-2H-pyrimidin-1-yl)propylamino]-1-phenylcyclohexanecarbonitrile;

1-benzyl-3-{3-[1-(4-fluoro-2-methoxyphenyl)piperidin-4-ylamino]propyl}-5-methyl-1H-pyrimidine-2,4-dione;

trans-1-benzyl-3-{3-[4-(2-methoxyphenyl)cyclohexylamino]propyl}-5-methyl-1H-pyrimidine-2,4-dione;

2-{4-[3-(3-benzyl-5-methyl-2,6-dioxo-3,6-dihydro-2H-pyrimidin-1-yl)propylamino]cyclohexyl}benzonitrile;

trans-2-{4-[3-(3-benzyl-2,6-dioxo-5-phenyl-3,6-dihydro-2H-pyrimidin-1-yl)propylamino]-1-cyanocyclohexyl}benzonitrile; and
pharmaceutically acceptable salts thereof.

9. The compound according to claim 7, wherein the compound is of formula

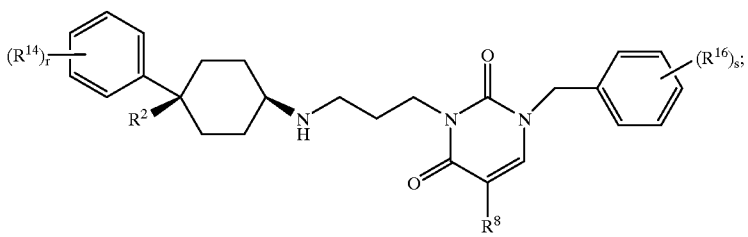

wherein $R^8$ is hydrogen, halo, cyano, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)R^c$, or $C(=O)N(R^c)_2$; or
a pharmaceutically acceptable salt thereof.

10. The compound according to claim 9, wherein the compound is selected from the group consisting of cis-4-[3-(3-benzyl-5-methyl-2,6-dioxo-3,6-dihydro-2H-pyrimidin-1-yl)propylamino]-1-(2,4-difluorophenyl)cyclohexanecarbonitrile;

cis-4-[3-(3-benzyl-5-methyl-2,6-dioxo-3,6-dihydro-2H-pyrimidin-1-yl)propylamino]-1-phenylcyclohexanecarbonitrile;

cis-4-[3-(3-benzyl-5-methyl-2,6-dioxo-3,6-dihydro-2H-pyrimidin-1-yl)propylamino]-1-(3,5-difluorophenyl)cyclohexanecarbonitrile;

cis-4-[3-(3-benzyl-5-methyl-2,6-dioxo-3,6-dihydro-2H-pyrimidin-1-yl)propylamino]-1-(2-methoxyphenyl)cyclohexanecarbonitrile;

cis-4-[3-(3-benzyl-5-methyl-2,6-dioxo-3,6-dihydro-2H-pyrimidin-1-yl)propylamino]-1-(2-trifluoromethylphenyl)cyclohexanecarbonitrile;

cis-4-[3-(3-benzyl-5-methyl-2,6-dioxo-3,6-dihydro-2H-pyrimidin-1-yl)propylamino]-1-(4-fluoro-2-trifluoromethylphenyl)cyclohexanecarbonitrile;

cis-4-[3-(3-benzyl-5-methyl-2,6-dioxo-3,6-dihydro-2H-pyrimidin-1-yl)propylamino]-1-(2,4-dichlorophenyl)cyclohexanecarbonitrile;

cis-2-{4-[3-(3-benzyl-5-methyl-2,6-dioxo-3,6-dihydro-2H-pyrimidin-1-yl)propylamino]-1-cyanocyclohexyl}benzonitrile;

cis-4-[3-(3-benzyl-5-methyl-2,6-dioxo-3,6-dihydro-2H-pyrimidin-1-yl)propylamino]-1-(2-trifluoromethoxyphenyl)cyclohexanecarbonitrile;

cis-4-[3-(3-benzyl-5-methyl-2,6-dioxo-3,6-dihydro-2H-pyrimidin-1-yl)propylamino]-1-pyridin-2-ylcyclohexanecarbonitrile;

cis-2-{4-[3-(3-benzyl-2,6-dioxo-5-phenyl-3,6-dihydro-2H-pyrimidin-1-yl)propylamino]-1-cyanocyclohexyl}benzonitrile; and
pharmaceutically acceptable salts thereof.

11. The compound according to claim 1, wherein the compound is of formula:

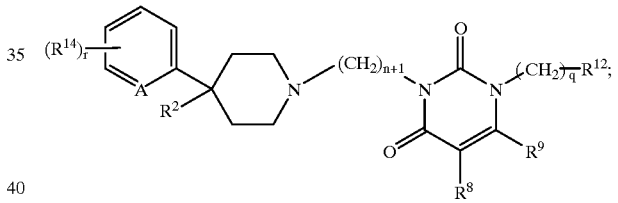

wherein A is C—$R^{14}$ or N;

$R^2$ is hydrogen, cyano, hydroxy, $CO_2R^c$, $C(=O)N(R^c)_2$, $NR^cC(=O)R^c$ or $NR^cSO_2R^c$;

$R^8$ and $R^9$ are each independently selected from hydrogen, halo, cyano, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)R^c$, $C(=O)N(R^c)_2$, phenyl, and mono- or di-substituted phenyl; wherein each substituent on the substituted phenyl is independently selected from fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ and $SO_2NH_2$;

$R^{12}$ is hydrogen, $C_1$–$C_4$ alkyl, $C_3$–$C_6$ cycloalkyl, $C_1$–$C_4$ alkoxy, fluorinated $C_1$–$C_4$ alkyl, fluorinated $C_1$–$C_4$ alkoxy, $CO_2R^c$, phenyl, or mono- or di-substituted phenyl; wherein each substituent on the substituted phenyl is independently selected from halo, nitro, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$;

each $R^{14}$ is independently hydrogen, halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ or $SO_2N(R^c)_2$;

$R^c$ is hydrogen or $C_1$–$C_4$ alkyl; and r is an integer of from 0 to 2;

or a pharmaceutically acceptable salt thereof.

12. The compound according to claim 11, wherein $R^{12}$ is of formula:

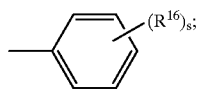

wherein each $R^{16}$ is independently hydrogen, fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ or $SO_2NH_2$;

q is 1; and s is an integer of from 0 to 2;

or a pharmaceutically acceptable salt thereof.

13. The compound according to claim 12, wherein the compound is selected from the group consisting of 1-benzyl-3-{3-[4-(4-fluorophenyl)piperidin-1-yl]propyl}-5-methyl-1H-pyrimidine-2,4-dione;

1-[3-(3-benzyl-5-methyl-2,6-dioxo-3,6-dihydro-2H-pyrimidin-1-yl)propyl]-4-ortho-tolylpiperidine-4-carbonitrile;

2-{1-[3-(3-benzyl-5-methyl-2,6-dioxo-3,6-dihydro-2H-pyrimidin-1-yl)propyl]piperidin-4-yl}benzonitrile; and pharmaceutically acceptable salts thereof.

14. The compound according to claim 1, wherein the compound is of formula

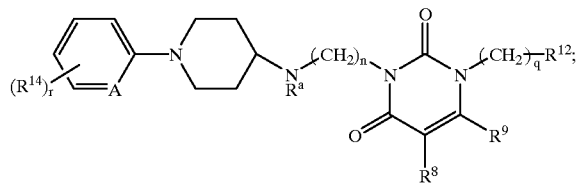

wherein A is C—$R^{14}$ or N;

$R^8$ and $R^9$ are each independently selected from hydrogen, halo, cyano, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)R^c$, $C(=O)N(R^c)_2$, phenyl, and mono- or di-substituted phenyl; wherein each substituent on the substituted phenyl is independently selected from fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ and $SO_2NH_2$;

$R^{12}$ is hydrogen, $C_1$–$C_4$ alkyl, $C_3$–$C_6$ cycloalkyl, $C_1$–$C_4$ alkoxy, fluorinated $C_1$–$C_4$ alkyl, fluorinated $C_1$–$C_4$ alkoxy, phenyl, or mono- or di-substituted phenyl; wherein each substituent on the substituted phenyl is independently selected from halo, nitro, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$;

each $R^{14}$ is independently hydrogen, halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ or $SO_2N(R^c)_2$;

$R^a$ is hydrogen or $C_1$–$C_6$ alkyl;

$R^c$ is hydrogen or $C_1$–$C_4$ alkyl; and r is an integer of from 0 to 2;

or a pharmaceutically acceptable salt thereof.

15. The compound according to claim 14, wherein the compound is 3-{3-[1-(4-fluoro-2-methoxyphenyl)piperidin-4-ylamino]propyl}-5-methyl-1H-pyrimidine-2,4-dione; or a pharmaceutically acceptable salt thereof.

16. The compound according to claim 14, wherein $R^{12}$ is of formula:

wherein each $R^{16}$ is independently hydrogen, fluoro, chloro, nitro, cyano, hydroxy, amino, methyl, ethlyl, methoxy, ethoxy, trifluromethyl, trifluoromethoxy, trifluoroethoxy, $CO_2CH_3$, $C(=O)NH_2$ or $SO_2NH_2$;

q is 1; and s is an integer of from 0 to 2;

or a pharmaceutically acceptable salt thereof.

17. The compound according to claim 1, wherein the compound is of formula:

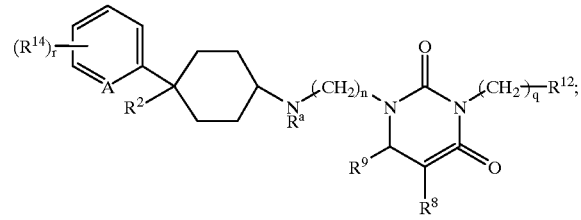

wherein A is C—$R^{14}$ or N;

$R^2$ is hydrogen, cyano, hydroxy, $CO_2R^c$, $C(=O)N(R^c)_2$, $NR^cC(=O)R^c$ or $NR^cSO_2R^c$;

$R^8$ and $R^9$ are each independently selected from hydrogen, halo, cyano, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)R^c$, $C(=O)N(R^c)_2$, phenyl, and mono- or di-substituted phenyl; wherein each substituent on the substituted phenyl is independently selected from fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ and $SO_2NH_2$;

$R^{12}$ is hydrogen, $C_1$–$C_4$ alkyl, $C_3$–$C_6$ cycloalkyl, $C_1$–$C_4$ alkoxy, fluorinated $C_1$–$C_4$ alkyl, fluorinated $C_1$–$C_4$ alkoxy, $CO_2R^c$, phenyl, or mono- or di-substituted phenyl; wherein each substituent on the substituted phenyl is independently selected from halo, nitro, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ and $SO_2N(R^c)_2$;

each $R^{14}$ is independently hydrogen, halo, cyano, hydroxy, amino, $C_1$–$C_4$ alkyl, $C_1$–$C_4$ alkoxy, fluorinated $C_1$–$C_4$ alkyl, fluorinated $C_1$–$C_4$ alkoxy, $CO_2R^c$, $C(=O)N(R^c)_2$ or $SO_2N(R^c)_2$;

$R^a$ is hydrogen or $C_1$–$C_6$ alkyl;

$R^c$ is hydrogen or $C_1$–$C_4$ alkyl; and r is an integer of from 0 to 2;

or a pharmaceutically acceptable salt thereof.

18. The compound according to claim 17, wherein $R^{12}$ is of formula:

wherein each $R^{16}$ is independently hydrogen, fluoro, chloro, nitro, cyano, hydroxy, amino, methyl, ethyl, methoxy, ethoxy, trifluromethyl, trifluoromethoxy, trifluoroethoxy, $CO_2CH_3$, $C(=O)NH_2$ or $SO_2NH_2$;

q is 1; and s is an integer of from 0 to 2;

or a pharmaceutically acceptable salt thereof.

19. The compound according to claim 18, wherein the compound is selected from the group consisting of cis-2-{4-[3-(3-benzyl-5-methyl-2,4-dioxo-3,4-dihydro-2H-pyrimidin-1-yl)propylamino]-1-cyanocyclohexyl}benzonitrile;

trans-2-{4-[3-(3-benzyl-5-methyl-2,4-dioxo-3,4-dihydro-2H-pyrimidin-1-yl)propylamino]-1-cyanocyclohexyl}benzonitrile; and pharmaceutically acceptable salts thereof.

20. A pharmaceutical composition comprising the compound according to claim 1 and a pharmaceutically acceptable carrier.

21. A pharmaceutical composition made by combining the compound according to claim 1 and a pharmaceutically acceptable carrier.

22. A process for making a pharmaceutical composition comprising combining the compound according to claim 1 and a pharmaceutically acceptable carrier.

23. The composition according to claim 20 further comprising a testosterone 5-alpha reductase inhibitor.

24. The composition according to claim 23, wherein the testosterone 5-alpha reductase inhibitor is a type 1, a type 2, both a type 1 and a type 2, or a dual type 1 and type 2 testosterone 5-alpha reductase inhibitor.

25. The composition according to claim 24, wherein the testosterone 5-alpha reductase inhibitor is a type 2 testosterone 5-alpha reductase inhibitor.

26. The composition according to claim 25, wherein the testosterone 5-alpha reductase inhibitor is finasteride.

27. A method of treating benign prostatic hyperplasia in a subject in need thereof which comprises administering to the subject a therapeutically effective amount of the compound according to claim 1.

28. The method according to claim 27, wherein the compound does not cause a fall in blood pressure at dosages effective to alleviate benign prostatic hyperlasia.

29. The method according to claim 27, wherein the compound is administered in combination with a testosterone 5-alpha reductase inhibitor.

30. The method according to claim 29, wherein the testosterone 5-alpha reductase inhibitor is finasteride.

31. A method of treating benign prostatic hyperplasia in a subject in need thereof which comprises administering a therapeutically effective amount of the composition according to claim 20.

32. The method according to claim 31, wherein the composition further comprises a therapeutically effective amount of a testosterone 5-alpha reductase inhibitor.

33. A method of relaxing lower urinary tract tissue in a subject in need thereof which comprises administering to the subject a therapeutically effective amount of the compound according to claim 1.

34. The method according to claim 33, wherein the compound is administered in combination with a testosterone 5-alpha reductase inhibitor.

35. The method according to claim 34, wherein the testosterone 5-alpha reductase inhibitor is finasteride.

36. A method of treating a condition which is susceptible to treatment by antagonism of the alpha 1a receptor which comprises administering to a subject in need thereof an amount of the compound according to claim 1 effective to treat the condition.

37. A method of eliciting an alpha 1a antagonizing effect in a mammal in need thereof, comprising administering to the mammal a therapeutically effective amount of the compound according to claim 1.

* * * * *